United States Patent
Larsen et al.

(10) Patent No.: US 9,376,655 B2
(45) Date of Patent: Jun. 28, 2016

(54) FILTER SYSTEMS FOR SEPARATING MICROCARRIERS FROM CELL CULTURE SOLUTIONS

(75) Inventors: Jeremy K. Larsen, Providence, UT (US); Jon Q. Coleman, Pleasant View, UT (US); David S. Rowley, Nibley, UT (US)

(73) Assignee: Life Technologies Corporation, Carlsbad, CA (US)

(*) Notice: Subject to any disclaimer, the term of this patent is extended or adjusted under 35 U.S.C. 154(b) by 1097 days.

(21) Appl. No.: 13/449,101

(22) Filed: Apr. 17, 2012

(65) Prior Publication Data

US 2013/0081995 A1 Apr. 4, 2013

Related U.S. Application Data

(60) Provisional application No. 61/540,967, filed on Sep. 29, 2011.

(51) Int. Cl.
*B01D 35/02* (2006.01)
*B01D 29/27* (2006.01)
(Continued)

(52) U.S. Cl.
CPC ............... *C12M 29/04* (2013.01); *B01D 29/27* (2013.01); *B01D 35/027* (2013.01); *C12M 23/14* (2013.01); *C12M 23/26* (2013.01); *C12M 25/16* (2013.01); *C12M 33/14* (2013.01); *C12M 47/02* (2013.01)

(58) Field of Classification Search
CPC ...... C12M 29/04; C12M 25/16; C12M 23/26; C12M 33/14; C12M 47/02; C12M 25/02; C12M 1/12; C12M 1/126; B01D 29/11; B01D 29/117; B01D 29/27; B01D 29/356; B01D 29/56; B01D 35/02; B01D 35/027; B01D 35/0273; B01D 35/0276; B01D 35/28; B01D 29/0029; B01D 29/0034; B01D 29/13; B01D 29/23; B01D 2201/04; B01D 2201/0415; B01D 2201/0423

USPC .............. 210/443, 448, 446, 451, 452, 257.1, 210/257.2, 321.6, 489, 499; 435/289.1, 435/297.1
See application file for complete search history.

(56) References Cited

U.S. PATENT DOCUMENTS 1,269,189 A 6/1918 Kadish
1,471,332 A 10/1923 Greenawalt
(Continued)

FOREIGN PATENT DOCUMENTS

CH 675368 A5 9/1990
DE 200 07 347 U1 8/2000
(Continued)

OTHER PUBLICATIONS

International Search Report and Written Opinion dated Jan. 2, 2013, issued in PCT/US2012/056917, filed Sep. 24, 2012.
(Continued)

*Primary Examiner* — Joseph Drodge
(74) *Attorney, Agent, or Firm* — Workman Nydegger

(57) ABSTRACT

A filter assembly for separating microcarriers from a fluid medium includes a collapsible container bounding a sterile compartment adapted to hold a fluid. An inlet port is attached to the container through which fluid flows into the compartment. An outlet port is attached to the container through which fluid flows out of the compartment. A filter is disposed within the compartment, the filter dividing the compartment into an inlet chamber that is fluidly coupled with the inlet port and an outlet chamber that is fluidly coupled with the outlet port, the filter allowing a medium to pass therethrough but preventing microcarriers disposed in the medium from passing therethrough.

20 Claims, 24 Drawing Sheets

(51) Int. Cl.
  *C12M 1/12* (2006.01)
  *C12M 1/00* (2006.01)
  *B01D 35/027* (2006.01)
  *C12M 1/26* (2006.01)

(56) References Cited

U.S. PATENT DOCUMENTS

| | | |
|---|---|---|
| 1,505,204 A | 8/1924 | Kiernan |
| 2,259,243 A | 10/1941 | Daman |
| 2,341,114 A * | 2/1944 | Novak .................. A61M 5/165 210/448 |
| 2,865,618 A | 12/1958 | Abell |
| 3,184,395 A | 5/1965 | Brewer |
| 3,647,397 A | 3/1972 | Coleman |
| 3,682,168 A | 8/1972 | Deaton |
| 3,701,433 A * | 10/1972 | Krakauer ............ A61M 1/3627 210/436 |
| 3,796,417 A | 3/1974 | Kaelin |
| 4,012,471 A | 3/1977 | Kunkle, Jr. |
| 4,012,473 A | 3/1977 | Lindsey et al. |
| 4,025,590 A | 5/1977 | Igich |
| 4,036,919 A | 7/1977 | Komendowski et al. |
| 4,061,698 A | 12/1977 | Thornwald |
| 4,100,235 A | 7/1978 | Thornwald |
| 4,157,965 A * | 6/1979 | Raible ........................... 210/305 |
| 4,204,774 A | 5/1980 | de Bruyne |
| 4,250,039 A * | 2/1981 | Cozzi et al. ................. 210/416.5 |
| 4,465,645 A | 8/1984 | Kaelin |
| 4,493,637 A | 1/1985 | Ganter et al. |
| 4,668,632 A | 5/1987 | Young et al. |
| 4,684,486 A | 8/1987 | Ricchio |
| 4,727,040 A | 2/1988 | Freedman et al. |
| 4,740,202 A | 4/1988 | Stacey et al. |
| 4,749,654 A | 6/1988 | Karrer et al. |
| 4,814,124 A | 3/1989 | Aoyama et al. |
| 4,869,852 A | 9/1989 | Goudy, Jr. et al. |
| 4,981,623 A | 1/1991 | Ryan |
| 5,008,197 A | 4/1991 | Wergeland et al. |
| 5,057,429 A | 10/1991 | Watanabe et al. |
| 5,183,595 A | 2/1993 | Schüssler |
| RE34,386 E | 9/1993 | Davidson et al. |
| 5,270,207 A | 12/1993 | Matsumura et al. |
| 5,376,271 A * | 12/1994 | Morgan, Jr. ............ B01D 29/23 210/450 |
| 5,422,043 A | 6/1995 | Burris |
| 5,443,985 A | 8/1995 | Lu et al. |
| 5,458,771 A | 10/1995 | Todd |
| 5,565,015 A | 10/1996 | Kobayashi |
| 5,578,459 A * | 11/1996 | Gordon .................... B01J 3/006 135/29 |
| 5,693,537 A | 12/1997 | Wilson et al. |
| 5,763,267 A * | 6/1998 | Kurjan .................... C12M 23/26 435/293.1 |
| 5,799,830 A | 9/1998 | Carroll et al. |
| 5,858,283 A | 1/1999 | Burris |
| 5,897,997 A | 4/1999 | Louvel |
| 5,941,635 A | 8/1999 | Stewart |
| 6,071,005 A | 6/2000 | Ekambaram et al. |
| 6,083,587 A | 7/2000 | Smith et al. |
| 6,086,574 A | 7/2000 | Carroll et al. |
| 6,117,801 A | 9/2000 | McGinty et al. |
| 6,186,932 B1 | 2/2001 | Vallot |
| 6,219,871 B1 | 4/2001 | Frederick et al. |
| 6,245,555 B1 | 6/2001 | Curtis |
| 6,250,796 B1 | 6/2001 | Huang |
| H1989 H | 9/2001 | Fell et al. |
| 6,367,783 B1 | 4/2002 | Raftis |
| 6,391,638 B1 | 5/2002 | Shaaltiel |
| 6,398,195 B1 | 6/2002 | Sherman |
| 6,406,005 B1 | 6/2002 | Lawson et al. |
| 6,432,698 B1 | 8/2002 | Gaugler et al. |
| 6,439,756 B1 | 8/2002 | Forschner et al. |
| 6,464,211 B1 | 10/2002 | Downs |
| 6,468,792 B1 | 10/2002 | Bader |
| 6,494,613 B2 | 12/2002 | Terentiev |
| 6,596,521 B1 | 7/2003 | Chang et al. |
| 6,632,658 B1 | 10/2003 | Schoeb |
| 6,649,405 B2 | 11/2003 | Alms et al. |
| 6,670,169 B1 | 12/2003 | Schöb et al. |
| 6,673,598 B1 | 1/2004 | Akers et al. |
| 6,709,862 B2 | 3/2004 | Curtis |
| 6,712,963 B2 * | 3/2004 | Schick ................. A61M 1/0209 210/137 |
| 6,884,866 B2 | 4/2005 | Bronshtein et al. |
| 6,908,223 B2 | 6/2005 | Bibbo et al. |
| 6,923,567 B2 | 8/2005 | Bibbo et al. |
| 7,141,203 B2 | 11/2006 | Way et al. |
| 7,198,255 B2 | 4/2007 | Chiba |
| 7,278,780 B2 | 10/2007 | Goodwin et al. |
| 7,326,355 B2 | 2/2008 | Graetz et al. |
| 7,384,027 B2 | 6/2008 | Terentiev et al. |
| 7,384,783 B2 | 6/2008 | Kunas et al. |
| 7,431,837 B2 | 10/2008 | Cohee et al. |
| 7,469,884 B2 | 12/2008 | Terentiev et al. |
| 7,629,167 B2 | 12/2009 | Hodge et al. |
| 7,681,867 B2 | 3/2010 | Hu et al. |
| 7,682,067 B2 | 3/2010 | West et al. |
| 8,282,267 B2 | 10/2012 | Castillo et al. |
| 2002/0063347 A1 | 5/2002 | Lee et al. |
| 2002/0131654 A1 | 9/2002 | Smith et al. |
| 2003/0077466 A1 | 4/2003 | Smith et al. |
| 2003/0119185 A1 | 6/2003 | Berenson et al. |
| 2004/0062140 A1 | 4/2004 | Cadogan et al. |
| 2004/0095842 A1 | 5/2004 | Weetman |
| 2005/0158851 A1 | 7/2005 | Furey |
| 2005/0218075 A1 * | 10/2005 | Graetz et al. ...................... 210/637 |
| 2005/0239199 A1 | 10/2005 | Kunas et al. |
| 2005/0272146 A1 | 12/2005 | Hodge et al. |
| 2005/0282269 A1 | 12/2005 | Proulx |
| 2006/0054557 A1 | 3/2006 | Hori et al. |
| 2006/0196501 A1 | 9/2006 | Bibbo et al. |
| 2006/0270036 A1 | 11/2006 | Goodwin et al. |
| 2008/0139865 A1 | 6/2008 | Galliher |
| 2008/0293133 A1 | 11/2008 | Reid et al. |
| 2009/0035856 A1 | 2/2009 | Galliher et al. |
| 2010/0078395 A1 | 4/2010 | Shevitz |
| 2011/0020922 A1 | 1/2011 | Wuenn et al. |
| 2012/0238011 A1 * | 9/2012 | Tuohey et al. .............. 435/297.1 |

FOREIGN PATENT DOCUMENTS

| | | |
|---|---|---|
| EP | 0 343 885 A1 | 11/1989 |
| EP | 1 602 715 A3 | 12/2005 |
| FR | 2 519 020 | 1/1983 |
| FR | 2 799 138 | 4/2001 |
| GB | 2 202 549 A | 9/1988 |
| JP | 50-119561 | 9/1975 |
| JP | 58-224683 | 12/1983 |
| JP | 61-067476 | 4/1986 |
| JP | 62-160899 | 7/1987 |
| JP | 2-31825 | 2/1990 |
| JP | 02-283274 | 11/1990 |
| JP | 03-010675 | 1/1991 |
| JP | 03-242297 | 10/1991 |
| JP | 05-336957 | 12/1993 |
| JP | 70-08264 | 1/1995 |
| JP | 07-155170 | 6/1995 |
| JP | 82-24076 | 9/1996 |
| JP | 10-099071 | 4/1998 |
| JP | 10-150972 | 9/1998 |
| JP | 10-313718 | 12/1998 |
| JP | 11-502716 | 9/1999 |
| JP | 11-299478 | 11/1999 |
| JP | 2001-258547 | 9/2001 |
| JP | 2002-101867 | 4/2002 |
| JP | 2007-511230 | 5/2007 |
| RU | 2 220 917 C1 | 1/2004 |
| WO | 96/30497 | 10/1996 |
| WO | 01/25394 | 4/2001 |
| WO | 02/41484 A2 | 5/2002 |
| WO | 2005/068059 A1 | 7/2005 |
| WO | 2005/118771 | 12/2005 |

(56) References Cited

FOREIGN PATENT DOCUMENTS

| WO | 2006/116067 | A1 | 11/2006 |
| WO | 2007/134267 | A2 | 11/2007 |
| WO | 2008/040568 | A1 | 4/2008 |
| WO | 2011/025890 | A1 | 3/2011 |
| WO | WO2011025890 | * | 3/2011 |

OTHER PUBLICATIONS

U.S. Appl. No. 60/577,143, filed Jun. 4, 2004 to Hodge.
DuPont Medical Packaging, Technical Reference Guide for Medical Packaging, The Miracles of Science, 2002.

* cited by examiner

FILTER SYSTEMS FOR SEPARATING MICROCARRIERS FROM CELL CULTURE SOLUTIONS

CROSS-REFERENCE TO RELATED APPLICATIONS

This application claims the benefit of U.S. Provisional Application No. 61/540,967, filed Sep. 29, 2011, which is incorporated herein by specific reference.

BACKGROUND OF THE INVENTION

1. The Field of the Invention

The present invention relates to filter systems and assemblies for separating microcarriers from cell culture solutions.

2. The Relevant Technology

The use of microcarriers in the biopharmaceutical industry is well known. Microcarriers can support the growth of anchorage-dependent cells thereon. Because of this, microcarriers are regularly used during cell culturing to optimize growth of various anchorage-dependent cell lines, such as protein-producing or virus-generating adherent cell populations, which are commonly used in the production of biologics (proteins) and vaccines.

Microcarriers have a surface chemistry that allows for attachment and growth of the anchorage dependent cells in cell culture procedures. Microcarriers can be made from a number of different materials and typically have a density that allows them to be maintained in suspension with gentle stirring.

Microcarrier cell culturing is typically carried out in a bioreactor. During culturing, the cells grow on the surface of the microcarriers. Once the cell culturing process is completed, the cultured cells are detached from the microcarriers through a chemical process carried out in the solution. The cultured solution containing the cells is then separated from the microcarriers for use or further processing. The gathered microcarriers can be cleaned, sterilized, and re-used, or can be discarded.

Separation of the microcarriers from the cultured solution that includes the detached cells is typically achieved by passing the solution through a rigid container having a horizontal screen that extends across the rigid container. The screen is a rigid mesh that allows the cultured fluid to pass through but prevents the microcarriers from doing so. However, as the microcarriers build up on the screen, they begin to clog the screen and prevent the fluid from passing therethrough. Once the screen is clogged, the process stops until the screen is unclogged. Furthermore, once the process is completed, the rigid container and related screen must be cleaned and sterilized before it can be reused. These process steps can be expensive and time consuming.

Accordingly, what is needed in the art are methods and/or systems that can alleviate one or more of the above problems.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope. In the drawings, like numerals designate like elements. Furthermore, multiple instances of an element may each include separate letters appended to the element number. For example two instances of a particular element "20" may be labeled as "20a" and "20b". In that case, the element label may be used without an appended letter (e.g., "20") to generally refer to every instance of the element; while the element label will include an appended letter (e.g., "20a") to refer to a specific instance of the element.

DETAILED DESCRIPTION OF THE PREFERRED EMBODIMENTS

As used in the specification and appended claims, directional terms, such as "top," "bottom," "left," "right," "up," "down," "upper," "lower," "proximal," "distal" and the like are used herein solely to indicate relative directions in viewing the drawings and are not intended to limit the scope of the claims in any way.

The present invention relates to various apparatuses and methods for effectively filtering microcarriers or other particulates out of a cell culture solution without clogging or otherwise impeding the flow of the solution away from the microcarriers.

Figure 1:
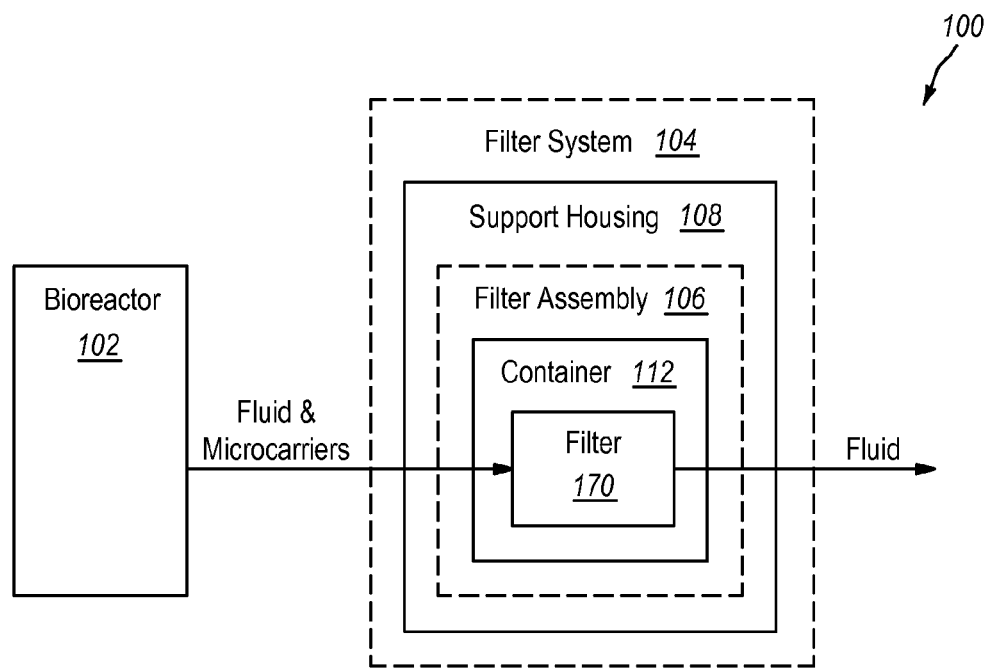
FIG. 1 is a block diagram of a cell culturing system that uses a filter system according to one embodiment.

FIG. 1 depicts a cell culturing system 100 that incorporates embodiments of the present invention. In cell culturing system 100, cells are grown within a biological container, such as bioreactor 102. Bioreactor 102 can be a microgravity bioreactor, internally-stirred bioreactor, fluidized bed bioreactor, rocker bag bioreactor or any other type of bioreactor known in the art. Bioreactor 102 can also be a rigid tank reactor that needs to be sterilized between uses or a single use bioreactor that includes a disposable bag. Other types of bioreactors or other biological containers can alternatively be used, such as, e.g., a spinner flask. The cells are grown in a nutrient growth medium that can include a variety of different components. The components are typically dependent on the cell type and processing conditions. Growth mediums and related components are known in the art and are not discussed herein.

Microcarriers are added to the growth medium within the bioreactor so that anchorage-dependent cells can grow thereon. The microcarriers can be spherically shaped beads ranging between about 130 microns to about 300 microns in diameter. Other sizes can also be used. It is also appreciated that the microcarriers can have alternative shapes but typically have a maximum diameter in a range between about 130 microns to about 300 microns. The microcarriers have a density that allows them to be maintained in suspension with gentle stirring. For example, the microcarriers can also have a density of about 1.02 g/cm$^3$ to about 1.10 g/cm$^3$. Other densities are also possible. The microcarriers can be made from a number of different materials including DEAE-dextran, glass, polystyrene plastic, acrylamide, and collagen. The different types of microcarriers can differ in their porosity, specific gravity, optical properties, presence of animal components, and surface chemistries. Surface chemistries can include extracellular matrix proteins, recombinant proteins, peptides, and positively or negatively charged molecules. The microcarrier materials, along with the different surface chemistries, can influence cellular behavior, including morphology, proliferation and adhesion.

During culturing, the cells grow on the surface of the microcarriers disposed within the mixture. Once the cell culturing process is completed, a chemical reagent, such as an enzyme, is added to the mixture, which includes the medium and the microcarriers suspended within the medium. The chemical reagent causes the cells to detach from the microcarriers so that the cells are freely suspended within the growth medium. The mixture is then removed from the bioreactor 102 and passed through a filter system 104. Filter system 104 includes a filter assembly 106 that can be housed in an optional support housing 108. The filter assembly 106 comprises a filter 170 disposed within a container 112. Filter 170 separates the microcarriers from the cultured solution, which includes the growth medium and the detached cells, by allowing the cultured solution to pass therethrough while preventing the microcarriers from doing so. Container 112 can be substantially rigid or flexible and can be disposable, if desired.

Figure 2:
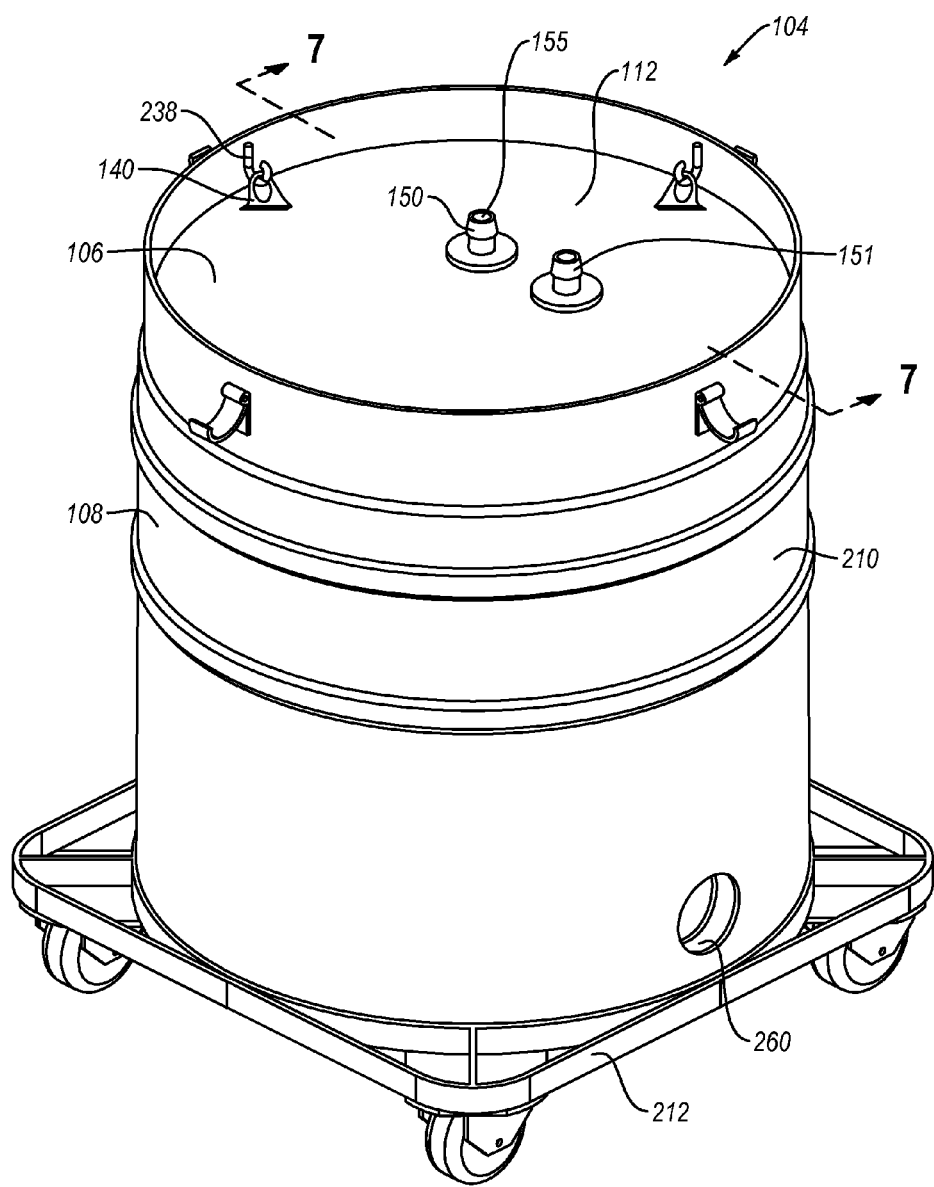
FIG. 2 is a perspective view of a filter system according to one embodiment.
Figure 3:
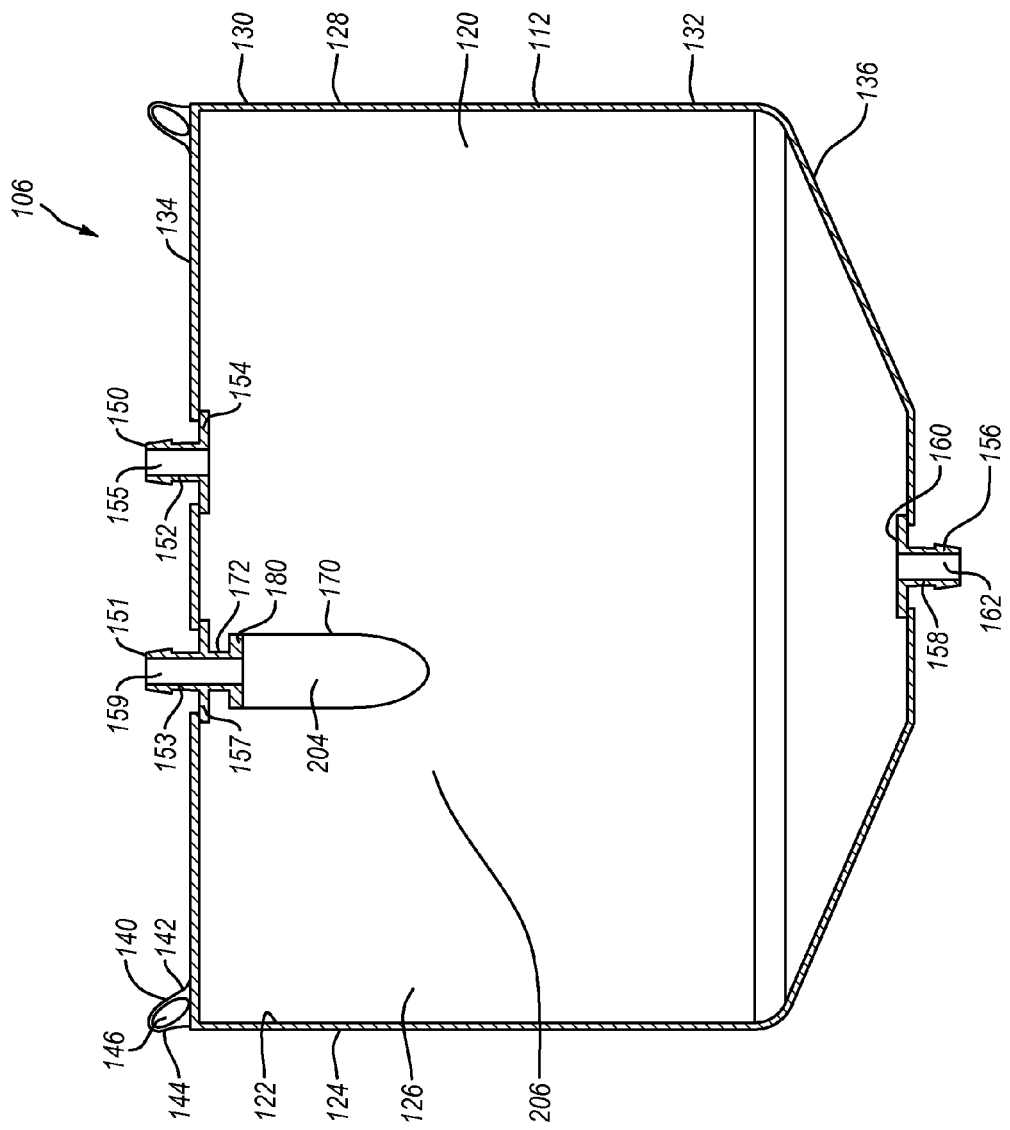
FIG. 3 is a cross sectional side view of the filter assembly of the filter system shown in FIG. 2.

FIG. 2 shows a perspective view of filter system 104 including support housing 108 and filter assembly 106. Depicted in FIG. 3 is a cross sectional side view of filter assembly 106. In part, filter assembly 106 includes container 112, a filter port 151 coupled to container 112 and filter 170 coupled to filter port 151. Filter assembly 106 can also include one or more inlet ports and an outlet ports through which fluid can flow into and out of container 112, respectively, as described in more detail below. In one embodiment, container 112 comprises a flexible and collapsible body 120, such as a flexible bag, having an interior surface 122 and an opposing exterior surface 124. Interior surface 122 bounds a compartment 126. More specifically, body 120 comprises a side wall 128 that, when body 120 is unfolded, has a substantially circular or polygonal transverse cross section that extends between a first end 130 and an opposing second end 132. First end 130 terminates at a top end wall 134 while second end 132 terminates at a bottom end wall 136.

Body 120 is comprised of a flexible, water impermeable material such as polyethylene or other polymeric sheets having a thickness in a range between about 0.1 mm to about 5 mm with about 0.2 mm to about 2 mm being more common. Other thicknesses can also be used. The material can be comprised of a single ply material or can comprise two or more layers which are either sealed together or separated to form a double wall container. Where the layers are sealed together, the material can comprise a laminated or extruded material. The laminated material comprises two or more separately formed layers that are subsequently secured together by an adhesive.

The extruded material comprises a single integral sheet that comprises two or more layers of different material that can be separated by a contact layer. All of the layers are simultaneously co-extruded. One example of an extruded material that can be used in the present invention is the HyQ CX3-9 film available from HyClone Laboratories, Inc. out of Logan, Utah. The HyQ CX3-9 film is a three-layer, 9 mil cast film produced in a cGMP facility. The outer layer is a polyester elastomer coextruded with an ultra-low density polyethylene product contact layer. Another example of an extruded material that can be used in the present invention is the HyQ CX5-14 cast film also available from HyClone Laboratories, Inc. The HyQ CX5-14 cast film comprises a polyester elastomer outer layer, an ultra-low density polyethylene contact layer, and an EVOH barrier layer disposed therebetween. In still another example, a multi-web film produced from three independent webs of blown film can be used. The two inner webs are each a 4 mil monolayer polyethylene film (which is referred to by HyClone as the HyQ BM1 film) while the outer barrier web is a 5.5 mil thick 6-layer coextrusion film (which is referred to by HyClone as the HyQ BX6 film).

The material is approved for direct contact with living cells and is capable of maintaining a solution sterile. In one embodiment, the material can be sterilizable such as by ionizing radiation or other conventional techniques. Other examples of materials that can be used in different situations are disclosed in U.S. Pat. No. 6,083,587 which issued on Jul. 4, 2000 and United States Patent Publication No. US 2003-0077466 A1, published Apr. 24, 2003 which are hereby incorporated by specific reference.

In one embodiment, body 120 comprises a two-dimensional pillow style bag wherein two sheets of material are placed in overlapping relation and the two sheets are bounded together at their peripheries to form internal compartment 126. Alternatively, a single sheet of material can be folded over and seamed around the periphery to form internal compartment 126. In another embodiment, body 120 can be formed from a continuous tubular extrusion of polymeric material that is cut to length and is seamed closed at the ends. In still other embodiments, such as in the depicted embodiment, body 120 comprises a three-dimensional bag that not only has an annular side wall 128 but also a two dimensional top end wall 134 and a two dimensional bottom end wall 136. Three dimensional containers can comprise a plurality of discrete panels, typically three or more, and more commonly four or six. Each panel can be substantially identical and can comprise a portion of the side wall, top end wall, and bottom end wall of the container. Corresponding perimeter edges of each panel can be seamed. The seams are typically formed using methods known in the art such as heat energies, RF energies, sonics, or other sealing energies.

In alternative embodiments, the panels can be formed in a variety of different patterns. Further disclosure with regard to one method of manufacturing three-dimensional bags is disclosed in United States Patent Publication No. US 2002-0131654 A1 that was published Sep. 19, 2002 of which the drawings and Detailed Description are hereby incorporated by reference.

Although in the above discussed embodiment body 120 is in the form of a flexible bag, in alternative embodiments it is appreciated that body 120 can also comprise any form of collapsible container or semi-rigid container. Body 120 can also be transparent or opaque and can have ultraviolet light inhibitors incorporated therein.

It is appreciated that body 120 can be manufactured to have virtually any desired size, shape, and configuration. For example, body 120 can be formed having compartment 126 that is sized to hold in a range from about 10 liters to about 2,000 liters, with about 20 liters to about 250 liters and about 20 liters to about 100 liters being more common. Other volume sizes can also be used. Although body 120 can be any shape, in one embodiment body 120 is specifically configured to be substantially complementary to a first chamber 232 (FIG. 6) of support housing 108, as discussed below.

Continuing with FIG. 3, one or more hanging tabs 140 can be mounted on top end wall 134 or the upper end of sidewall 128 to support the upper end of body 120 within support housing 108, if used. For example, in the depicted embodiment a plurality of radially spaced apart hanging tabs 140 are positioned on top end wall 134 at or near the outer perimeter thereof. Each hanging tab 140 includes a first end 142 secured to body 120 and an opposing second end 144 through which an opening 146 is formed. As shown in FIG. 2, when filter assembly 106 is positioned within support housing 108, a hanger 238 can be received within a corresponding opening 146 of each hanging tab 140 to support container 112 within support housing 108.

Hanging tabs 140 can be attached to body 120 or integrally formed therewith. Hanging tabs 140 can be made of the same material as body 120, if desired. In embodiments in which body 120 is comprised of panels, hanging tabs 140 can be attached to body 120 by being welded between the panels. In other embodiments, hanging tabs 140 can be mounted on the outside of body 120 such as by welding or adhesion.

As shown in FIG. 3, one or more inlet ports can be mounted on top end wall 134 of body 120. In the depicted embodiment, an inlet port 150 is shown. Inlet port 150 comprises a barbed tubular stem 152 having a flange 154 radially encircling and outwardly projecting therefrom. Inlet port 150 bounds a fluid passageway 155 that extends therethrough. During assembly, a hole is made through top end wall 134 for the port. The stem 152 of port 150 is then passed through the hole until flange 154 rests against top end wall 134. Conventional welding or other sealing techniques are then used to seal each flange 154 to top end wall 134. During use, stem 152 can be selectively coupled with a tube or container for delivering material into and/or out of compartment 126.

Mounted on bottom end wall 136 of body 120 is an outlet port 156. Similar to inlet port 150, outlet port 156 comprises a barbed tubular stem 158 having a flange 160 radially encircling and outwardly projecting therefrom. Outlet port bounds a fluid passageway 162 that extends therethrough. As with inlet ports 150, during assembly a hole is formed in bottom end wall 136. Outlet port 156 is seated within the hole so that flange 160 rests against bottom end wall 136. Again, conventional welding or other sealing technique is then used to seal flange 160 to bottom end wall 136. During use, stem 158 is selectively coupled with an outlet tube for delivering material out of compartment 126.

It is appreciated that any number of inlet ports 150 or outlet ports 156 can be formed on body 120 and that a variety of different types and sizes of ports can be used depending on the type of material to be dispensed into compartment 126 and how the material is to be dispensed therefrom. The ports 150 and 156 can also be located at different locations on body 120 such as side wall 128.

Figure 4:
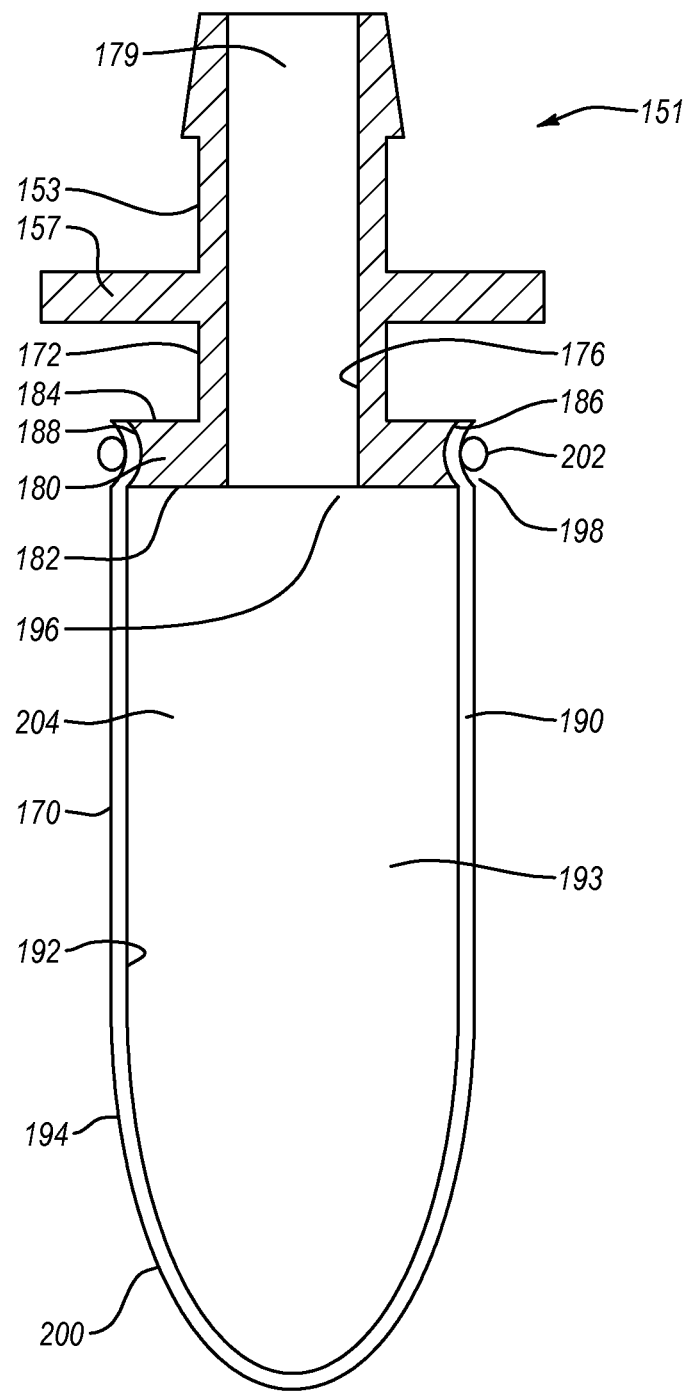
FIG. 4 is a cross sectional side view of the filter port and filter shown in FIG. 3.

Filter port 151 also functions as an inlet port. Specifically filter port 151 includes a flange 153 mounted to top end wall 134. A tubular first stem 153 upwardly projects from one side of flange 157 and has an annular barb formed on the end thereof. A tubular second stem 172 projects from an opposing side of flange 157 so as to extend downward into compartment 126. A support flange 180 encircles and radially outwardly projects from the end of second stem 172. Turning to FIG. 4, filter port 151 has an inside surface 176 that bounds a fluid passageway 179 extending therethrough, i.e., fluid passageway 179 extends through first stem 153, flange 157, second stem 172 and support flange 180. Filter port 151 can be integrally formed as a single unitary structure or can comprise two or more parts secured together. Support flange 180 has a lower face 182 and an opposing upper face 184 that both radially extend to an outside face 186. An annular groove 188 can be recessed on outside face 186 for mounting filter 170 thereto, as discussed below.

Filter 170 comprises a body 190 having an interior surface 192 that bounds a compartment 193 and an opposing exterior surface 194. A mouth 196 is formed on body 190 so as to communicate with compartment 193. In one embodiment, filter 170 is flexible and can be in the form of a porous bag or sock. Filter 170 is attached to filter port 151 by inserting support flange 180 within mouth 196. A connector 202 such as a clamp, cable tie crimp ring, strap, or the like is then positioned over filter 170 and tightened so as to secure filter 170 within groove 188. In alternative embodiments, it is appreciated that other conventional methods can be used to secure filter 170 to filter port 151. For example, filter 170 can be secured to filter port 151 by welding, adhesive or the like. In other embodiments, support flange 180 can be eliminated and filter 170 can be attached directly to second stem 172. In still other embodiments, support flange 180 and second stem 172 can both be eliminated and filter 170 can be attached to an extended version of flange 157.

Lower surface 182 of support flange 180 and interior surface 192 of filter 170 together bound an inlet chamber 204 that is fluidly coupled with fluid passageway 179. As discussed below in greater detail, during use a mixture of cultured solution and associated microcarriers can be delivered to inlet chamber 204 through filter port 151. Filter 170 comprises a material that will allow the cultured solution to pass therethrough while preventing the microcarriers from passing therethrough. As such, the microcarrier are collected within inlet chamber 204 of body 190. Filter 170 can be comprised of a porous material, such as a mesh, netting, perforated sheets, lattice type of material, or any other material that will allow the cultured solution to pass therethrough while preventing the associated microcarriers from passing therethrough. To enable the cells to pass therethrough but prevent the microcarriers from passing therethrough, filter 170 is typically made of a material, having pores in the size of about 15 microns to about 100 microns, with about 30 microns to about 100 microns being common. If desired, filter 170 can be expandable and/or resiliently stretchable. Examples of materials that can be used for filter 170 include polyester (PET), polyamide (PA), polypropylene (PP), and polyetheretherketone (PEEK). Other materials can also be used.

In alternative embodiments, it is appreciated that part or all of filter 170 can be rigid or semi-rigid. For example, filter 170 can comprise body 190 formed from a porous flexible material while a rigid ring is mounted to body 160 and encircles mouth 196. The rigid ring could then be used to secure filter 170 to filter port 151 such as by threaded connection, bayonet connection, snap fit connection, press fit engagement, crimped engagement or the like. In other embodiments, filter 170 can be comprised of a rigid material. For example, filter 170 can be molded from a plastic, metal, or composite material, that has holes formed therethrough through which the cultured fluid can pass but the microcarriers cannot.

Returning to FIG. 3, as a result of filter 170 being coupled with filter port 151 which is attached to top end wall 134, filter 170 is suspended down into compartment 126. When disposed within compartment 126, filter 170 essentially divides compartment 126 into two chambers—inlet chamber 204 of filter 170, and an outlet chamber 206. Outlet chamber 206 is the portion of compartment 126 external to inlet chamber 204 and fluid passageway 178. As such, fluid flows from inlet chamber 204 to outlet chamber 206 through filter 170.

In one embodiment, filter 170 is sized and positioned so as to be suspended above bottom end wall 136 of container 112 and away from sidewall 128, as shown in FIG. 3. In some embodiments it can be desirable to keep filter 170 away from bottom end wall 136 and side wall 128 since contacting filter 170 against a structure can cause blocking of that portion of filter 170 which can decrease fluid flow through filter 170. In some embodiments, filter 170 remains above bottom end wall 136 during use so as to not contact bottom end wall 136. In other embodiments, filter 170 may contact bottom end wall 136 and/or side wall 128 such as after a portion of the microcarriers have been collected.

If an expandable material is used for filter 170, the weight of the microcarriers may cause filter 170 to expand downward and outward as more microcarriers are received, as discussed below. However, by being suspended from top end wall 134, filter 170 can in some embodiments be configured to remain above bottom end wall 136 even when expanded, as discussed in more detail below.

Support housing 108 can be used to support filter assembly 106 or any of the filter assemblies discussed herein. This can be especially helpful if container 112 is flexible, as support housing 108 can provide rigid support for container 112. Returning to FIG. 2, support housing 108 generally includes a substantially rigid receptacle 210 seated on a dolly 212. As depicted, receptacle 210 is configured to receive and support filter assembly 106.

Figure 5:
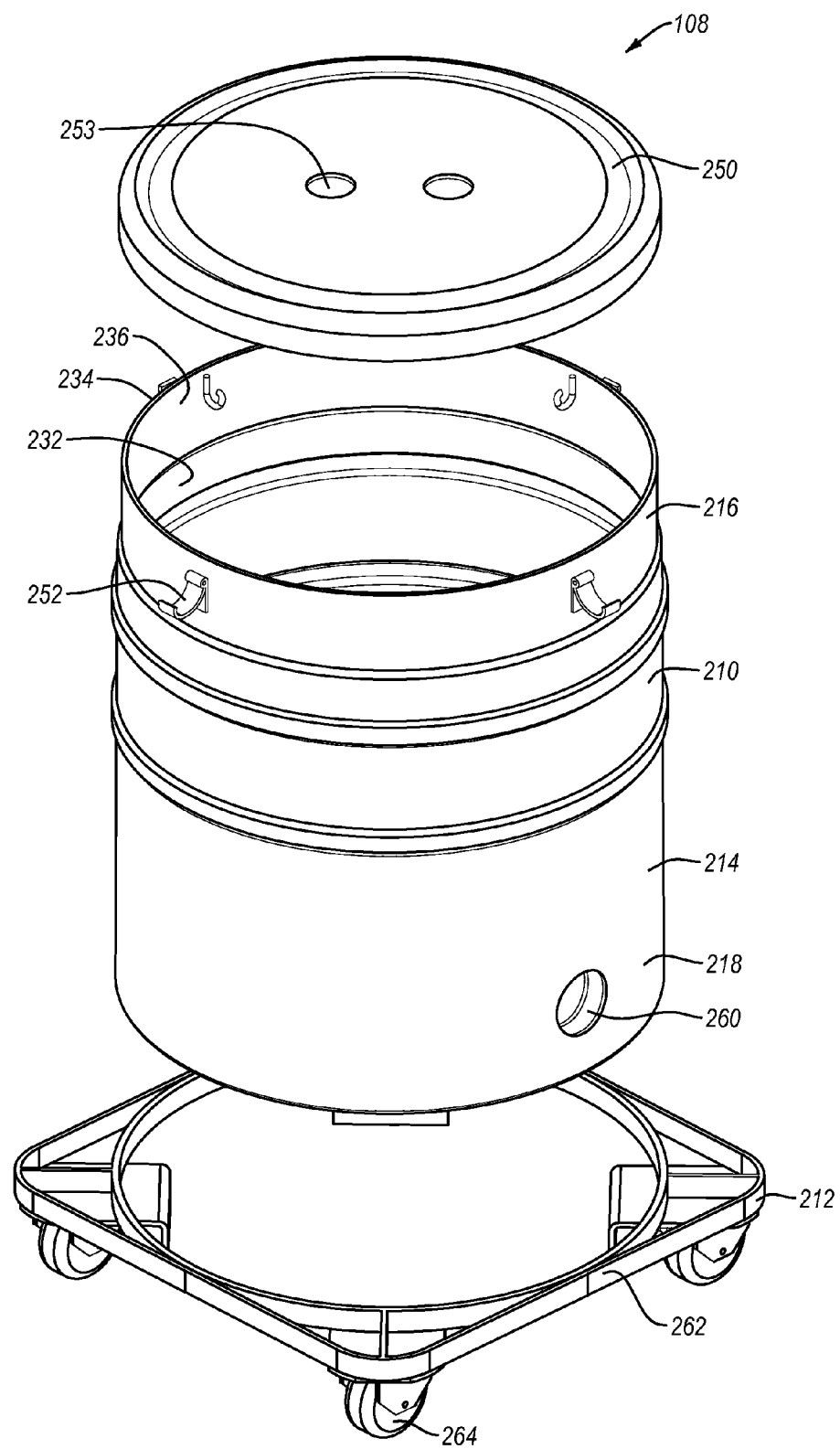
FIG. 5 is a perspective view of the support housing of the filter system shown in FIG. 2.
Figure 6:
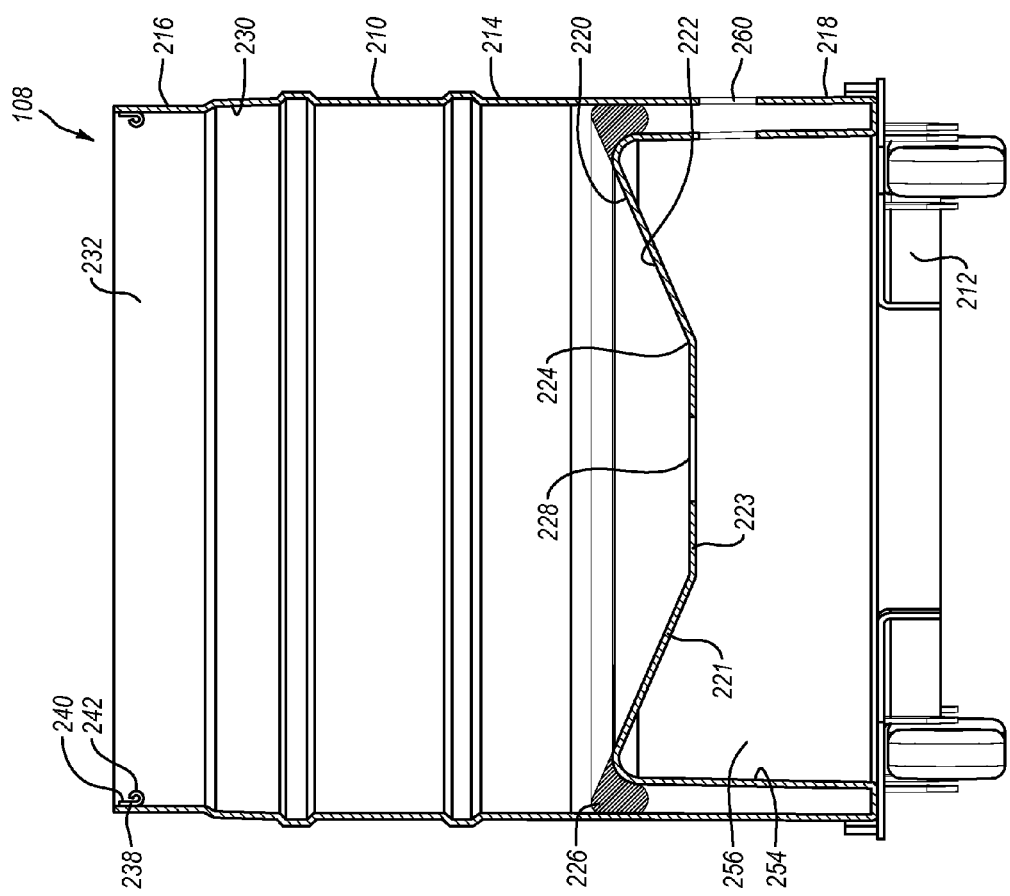
FIG. 6 is a cross sectional side view of the support housing of the filter system shown in FIG. 2.

Turning to FIGS. 5 and 6, receptacle 210 comprises a substantially cylindrical side wall 214 that extends from an upper end 216 to an opposing lower end 218. As depicted in FIG. 6, receptacle 210 includes a floor 220 formed inside of receptacle 210 at a position between upper end 216 and lower end 218. Floor 220 has a substantially frustoconical configuration. More specifically, floor 220 has a frustoconical portion 221 with a top surface 222 that extends between an inner edge 224 and an opposing outer edge 226. Floor 220 also includes a flat base portion 223 inwardly extending from frustoconical portion 221. Base portion 223 bounds a central opening 228 extending through floor 220. Outer edge 226 is integrally formed with or is otherwise connected to side wall 214. The slope of floor 220 functions in part as a funnel to direct all material toward central opening 228. In alternative embodiments, floor 220 can be flat, cupped, irregular, or other desired configurations.

Side wall 214 of receptacle 210 has an interior surface 230 disposed above floor 220. Interior surface 230 and floor 220 bound first chamber 232 formed in upper end 216 of receptacle 210. First chamber 232 is sized to receive container 112 and can thus have a corresponding size. Depicted in FIG. 5, upper end 216 of receptacle 210 terminates at an upper edge 234 that bounds an opening 236 to first chamber 232.

As shown in FIG. 5, an optional annular lid 250 can be removably disposed over upper edge 234 so as to selectively close opening 236. Clamps 252 can be used to selectively secure lid 250 to receptacle 210. Lid 250 can include one or more holes 253 extending therethrough. Holes 253 can be configured to align with ports 150 and 151 of container 112 so that inlet tubes can extend therethrough to attach to ports 150 and 151 and pass fluid into filter assembly 106.

As previously mentioned, one or more hangers 238 can be secured to lid 250 or sidewall 214 of receptacle 210 at or near upper edge 234 to receive the corresponding hanging tabs 140 of filter assembly 106. For example, as shown in FIG. 6, hangers 238 can be in the form of hooks positioned on interior surface 230 to receive hanging tabs 140 positioned on container 112, as shown in FIG. 2. As shown in FIG. 2, each hanger 238 is positioned on interior surface 230 so as to correspond to the position of one of the hanging tabs 140 when filter assembly 106 is positioned within first chamber 232. Hangers 238 can be attached to receptacle 210 by using screws, adhesive, welding or other known attachment methods.

When it is desired to remove filter assembly 106 from support housing 108, hanging tabs 140 can simply be disconnected from hangers 238 to allow filter assembly 106 to be removed. It is appreciated that hangers 238 can come in a variety of different forms. For example, hangers 238 can comprise hook that connect to hanging tabs 140 and then catches directly onto edge 234 of receptacle 210 for supporting filter assembly 106. In this embodiment, hangers are not fixed to receptacle 210. In still other embodiments, hangers 238 can comprise hooks or other types of projections or fasteners that are mounted on the exterior surface of sidewall 214. In this embodiment, hanging tabs 240 can pass over edge 234 and then connect to hangers 238.

Figure 18:
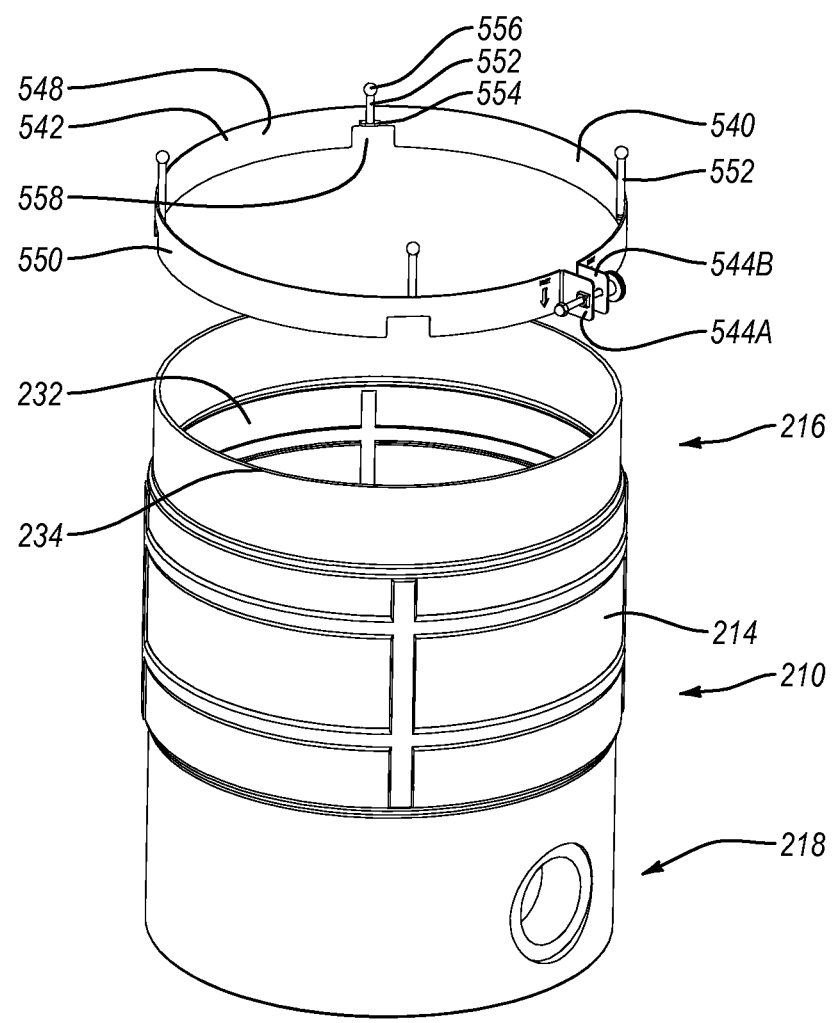
FIG. 18 is an exploded perspective view of a retention ring having hangers formed thereon and a related support housing.

Depicted in FIG. 18 is another alternative embodiment for the hangers. Specifically, a retention ring 540 is used for supporting container 112 within first chamber 232 of receptacle 210. Retention ring 540 comprises a substantially C-shaped ring body 542 that terminates at opposing ends having flanges 544A and 544B formed thereat. A fastener 546 extends through flanges 544A and B and can be used for selectively drawing and securing flanges 544A and B together. In one embodiment, fastener 546 can comprise a bolt and nut assembly. In alternative embodiments, fastener 546 can comprise a clamp, latch, or any other conventional fastener that achieves the desired objective.

Ring body 542 is typically in the form of a narrow band having an inside face 548 and an opposing outside face 550. A plurality of spaced apart hangers 552 are mounted on inside face 548 of ring body 542. In one embodiment, each hanger 552 comprises a elongated pin having a first end 554 that is secured, such as by welding, at a central location on inside face 548. Each pin also comprises an opposing second end 556 that projects up above ring body 540. If desired, second end 556 of each pin can be rounded. Although not required, in one embodiment a plurality of spaced apart notches 558 are recessed on the bottom edge of ring body 542 such that the top of each notch 558 is disposed adjacent to first end 554 of a corresponding hanger 552.

During use, fastener 546 is loosened so as to expand the size of ring body 542. Ring body 542 is then positioned on upper end 476 of receptacle 210 so that ring body 542 encircles the exterior surface of side wall 214 at upper end 216. In this configuration, first end 554 of each hanger 552 rests on top of upper edge 234 of side wall 214 so that retention ring 540 is properly positioned. If desired, a flange can be formed at first end 554 of each hanger 552 for receiving upper edge 234. Notches 558 permit a visual inspection to ensure that ring body 542 is properly seated. Fastener 546 is then used to clamp retention ring 540 on side wall 214. As container 112 (FIG. 3) is inserted within first chamber 232, second end 556 of each hanger 552 is passed through opening 146 of a corresponding hanging tab 140 (FIG. 3) so that container 112 is supported within first chamber 232.

In still other embodiments hangers 238 can be in the form of microhook and loop systems (commonly known as VELCRO), threaded connections, clamps, or the like that connect hanging tabs 140 to receptacle 210.

As shown in FIG. 6, side wall 214 also has an interior surface 254 formed below floor 220. Interior surface 254 and floor 220 bound a second chamber 256 disposed at lower end 218 of receptacle 210. An access port 260 extends through side wall 214 at lower end 218 of receptacle 210 so as to provide side access to second chamber 256. In alternative embodiments, the portion of side wall 214 extending below floor 220 can be replaced with one or more spaced-apart legs or other supports that elevate floor 220 off of the ground, dolly 212, or other surface on which receptacle 210 rests.

In the embodiment depicted, receptacle 210 comprises a barrel molded from a polymeric material. In alternative embodiments, receptacle 210 can be comprised of metal, fiberglass, composites, or any other desired material. Furthermore, although receptacle 210 is shown as having a substantially cylindrical configuration, receptacle 210 can be substantially boxed shaped or have a transverse configuration that is polygonal, elliptical, irregular, or any other desired configuration.

As depicted in FIG. 5, dolly 212 comprises a frame 262 having a plurality of wheels 264 mounted thereon. Dolly 212 enables easy movement of receptacle 210. In alternative embodiments where it is not necessary or desired to move receptacle 210, wheels 264 and/or frame 262 can be eliminated. In this regard, receptacle 210 can sit on a ground surface or any other desired structure. As shown in FIG. 6, lower end 218 of receptacle 210 is received on dolly 212 so as to be stably supported thereby.

Figure 7:
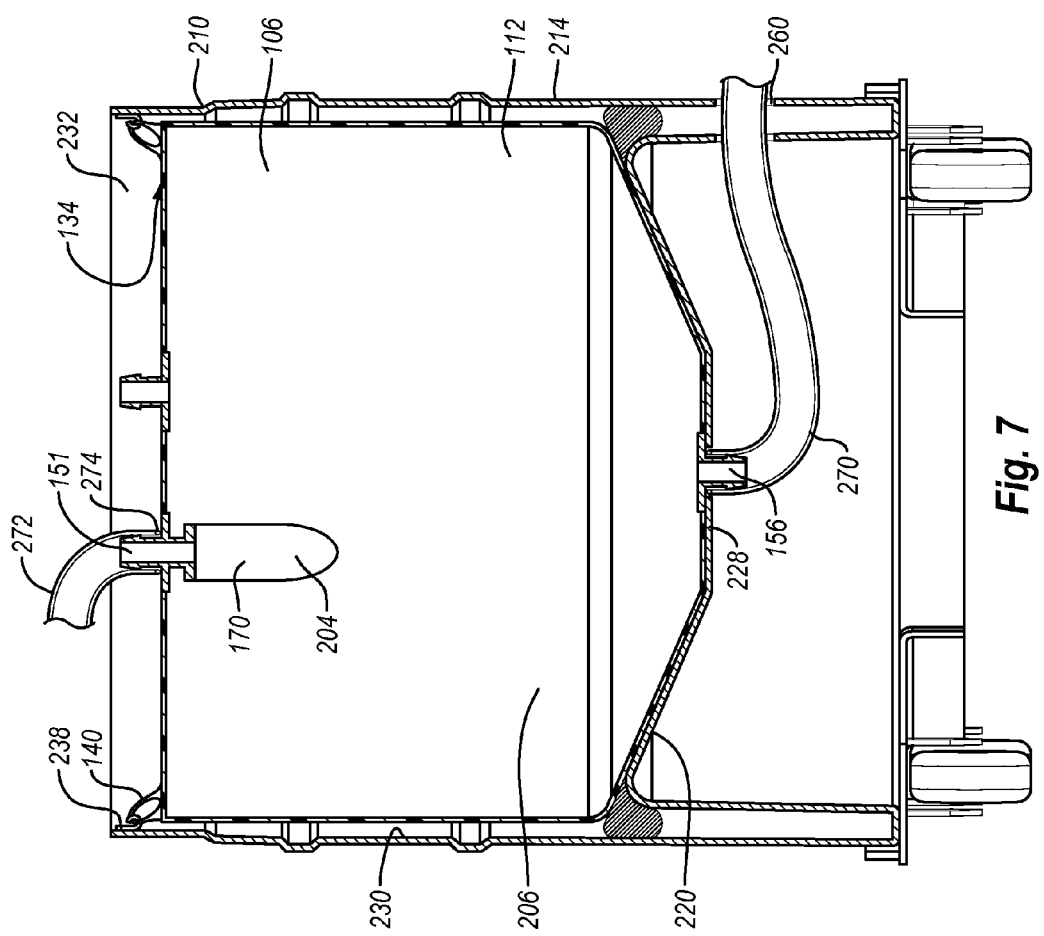
FIG. 7 is a cross sectional view of the filter system shown in FIG. 2 taken along section line 7-7 of FIG. 2.

Before use, filter assembly 106 can be positioned within first chamber 232 of receptacle 210 so that outlet port 156 can be received within central opening 228 extending through floor 220 of receptacle 210, as depicted in FIG. 7.

It is typically desirable that when filter assembly 106 is received within first chamber 232, container 112 is at least generally uniformly supported by floor 220 and side wall 214 of receptacle 210 when container 112 is at least partially filled with a fluid. Having at least general uniform support of container 112 by receptacle 210 helps to preclude failure of container 112 by hydraulic forces applied to container 112 when filled with a solution.

Hanging tabs 140 disposed on top end wall 134 are looped over hangers 238 disposed on interior surface 230 of receptacle 210 to suspend container 112 within first chamber 232. As such, container 112 may not extend all the way down to floor 220 until fluid is introduced into container 112. Before container 112 is disposed within first chamber 232, an outlet tube 270 can be connected to outlet port 156. Outlet tube 270 extends through central opening 228 and can extend out from support housing 108 through access port 260.

As noted above, filter 170 is suspended from top end wall 134 of container 112 by virtue of its coupling with filter port 151. Because filter 170 is indirectly attached to top end wall 134, filter 170 is generally suspended above bottom end wall 136 of container, as shown in FIG. 7.

An inlet tube 272 is coupled with first stem 153 of filter port 151. Either before or after filter assembly 106 has been positioned within first chamber 232, inlet tube 272 can be coupled in a sterile fashion with bioreactor 102 (FIG. 1). During use, a mixture of the cultured solution and the associated microcarriers from bioreactor 102 is introduced into inlet chamber 204 of filter assembly 106 through inlet tube 272. The cultured solution of the mixture, including the detached cells, passes through filter 170 and into outlet chamber 206.

Figures 8A, 8B, 8C:
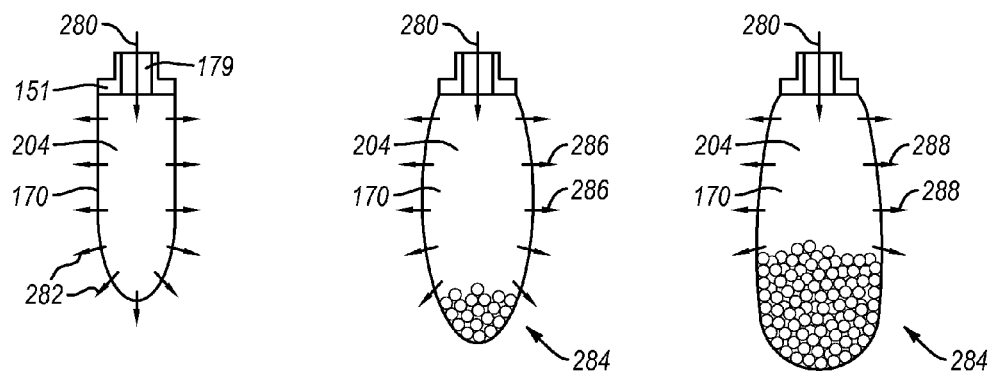
FIGS. 8A-8C are cross sectional side views of the filter and a portion of the filter port of the filter system shown in FIG. 2, showing fluid flow through the filter during various stages of use.

More specifically, the mixture passes through fluid passageway 179 in filter port 151 and is received by inlet chamber 204 of filter 170, as depicted in FIGS. 8A-8C. As shown in FIG. 8A, as the mixture is first received within inlet chamber 204, as denoted by arrow 280, inlet chamber 204 is completely or mostly devoid of microcarriers and the cultured solution can freely pass through filter 170 through the sides and bottom thereof, as indicated by arrows 282. As shown in FIGS. 8B and 8C, as more mixture flows into inlet chamber 204, the microcarriers (shown as a group of beads 284) within the mixture are retained and begin to accumulate at the bottom of inlet chamber 204. The cultured solution continues to pass through filter 170. However, the majority of the fluid passes out through the side portion of filter 170 that is above the accumulated microcarriers, as shown by arrows 286 and 288 in FIGS. 8B and 8C. This is because the accumulated microcarriers at least partially block the flow of fluid through the portion of filter 170 that they rest against. Thus, the configuration of filter 170 permits an efficient collection of microcarriers while still permitting a free flow of cultured solution through filter 170.

Filter 170 is typically sized so that all of the microcarriers from bioreactor 102 can be collected within inlet chamber 204 while still allowing a portion of filter 170 to be unobstructed by microcarriers so that the cultured solution can freely pass therethrough. Alternatively, a filter assembly 106 can be used until inlet chamber 204 is sufficiently filled with microcarriers that the cultured fluid can no longer pass through filter 170 as a desired processing rate. Filter assembly 106 can then be replaced with a new filter assembly 106 and the process continued.

If an expandable material is used for filter 170, the weight of the microcarriers can cause filter 170 to expand downward and outward, as depicted in FIGS. 8B and 8C. This expansion can cause filter 170 to become more elongate, thereby increasing the surface area of filter 170 and allowing more cultured solution to flow through the sides of filter 170 as to enable more microcarriers to be retained within inlet chamber 204.

After the cultured solution passes through filter 170, the cultured solution can either be retained within outlet chamber 206 or can pass directly out of container 112 through outlet port 156 and outlet tube 270. Once all of the cultured solution has been processed through filter assembly 106, filter assembly 106 can be removed from support housing 108 and discarded with the microcarriers contained therein. Alternatively, filter assembly 106 can be cut open and the microcarriers removed and recycled for further use. By forming filter assembly 106 from a disposable container and filter, the inventive system eliminates the need for cleaning or sterilizing the filtering system between different batches of culturing solution.

Figure 9:
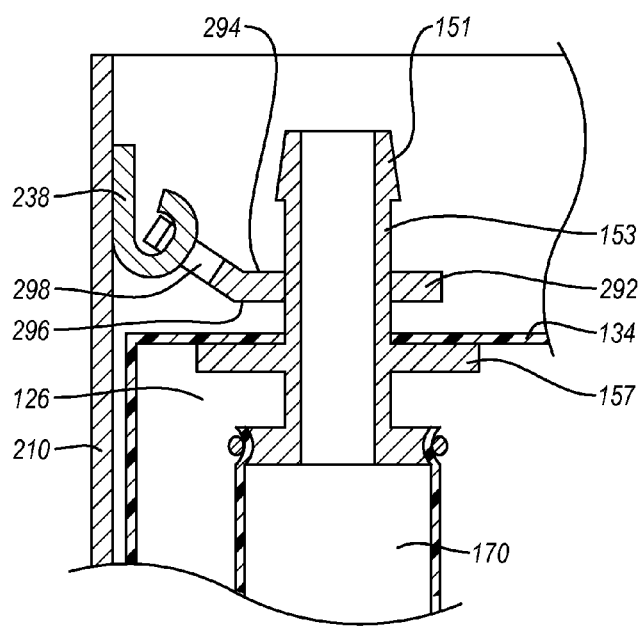
FIG. 9 is a cross sectional side view of a portion of a filter system showing one embodiment of a filter port that can be directly attached to the support housing.

In some systems, the weight of the microcarriers combined with the force caused by the downward motion of the incoming mixture can cause a strain on container 112 where filter port 151 attaches to top end wall 134. To alleviate this strain between filter port 151 and top end wall 134, filter port 151 can also be directly attached to receptacle 210 instead of or in conjunction with the hanging tabs and hangers, discussed above. For example, in the embodiment shown in FIG. 9, a hanging flange 292 is attached to or is integrally formed with stem 153 of filter port 151. Hanging flange 292 outwardly projects from stem 153 above flange 157 so that hanging flange 292 will be positioned outside of compartment 126 when filter port 151 has been attached to top end wall 134. Hanging flange 292 has a top surface 294 and an opposing bottom surface 296 and bounds an opening 298 extending therethrough. Similar to hanging tabs 140, discussed previously, opening 298 of hanging flange 292 can be looped over one of hangers 238 disposed on receptacle 210 to suspend filter port 151 and filter 170 from the top end of receptacle 210. To position opening 298 of hanging flange 292 adjacent to a hanger 238, filter port 151 can be positioned adjacent to the perimeter edge of top end wall 134, as shown in the depicted embodiment.

All or portions of hanging flange 292 can be flexible or substantially rigid. If hanging flange 292 is substantially rigid, the portion of hanging flange 292 that includes opening 298 can be shaped to form an angle with respect to the rest of second flange 292, as shown in the depicted embodiment, to more easily facilitate the attachment of hanging flange 292 to hanger 238 and to help keep filter 170 vertical. It is appreciated that all of the other methods as discussed above for securing hanging tabs 140 to receptacle 210 can also be used to secure hanging flange 292 to receptacle 210.

Figure 10A:
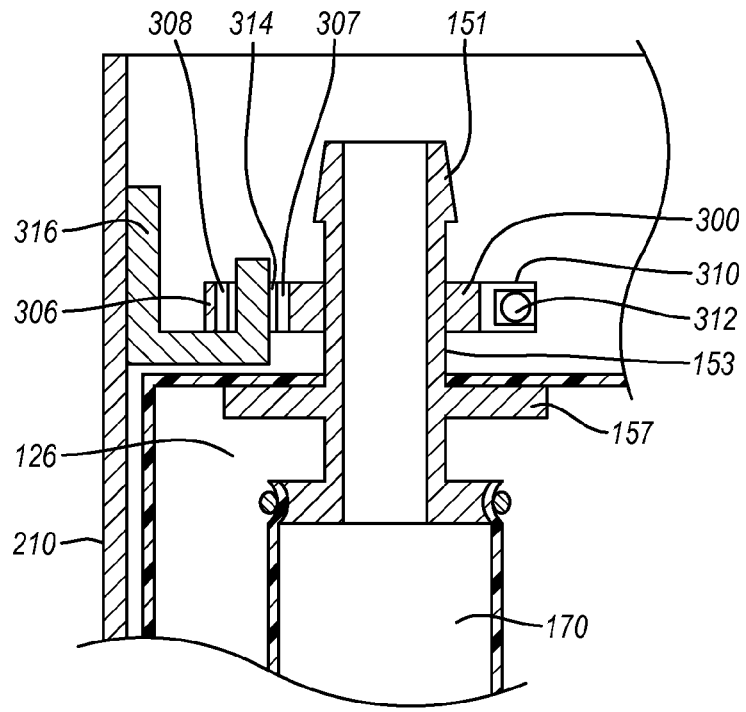
FIG. 10A is a cross sectional side view of a portion of a filter system showing another embodiment of a filter port directly attached to the support housing.
Figure 10B:
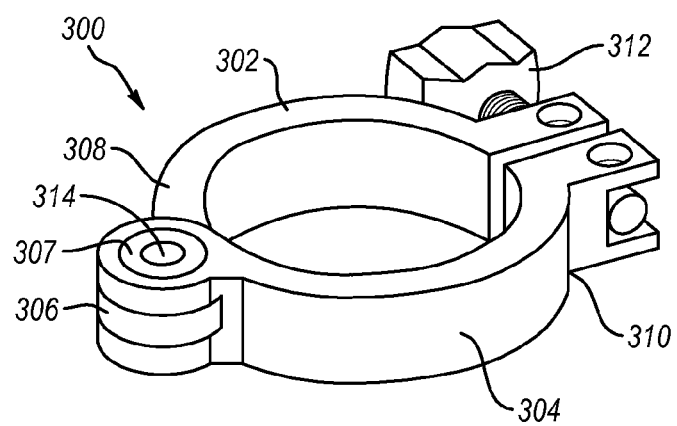
FIG. 10B is a perspective view of the clamp assembly of the filter system shown in FIG. 10A.

In one embodiment, the hanging flange 292 is replaced by an attachment device that is removable and reusable. For example, as shown in FIGS. 10A and 10B, the hanging flange 292 can be replaced by a clamp assembly 300 that removably attaches to stem 153. Clamp assembly 300 includes a pair of mating arms 302 and 304 that rotate about a hinge 306 positioned at one end 308 of the pair of arms. Hinge 306 includes a tubular hinge pin 307 that bounds an opening 314. At the other end 310 of arms 302/304 is a securing mechanism, such as a screw assembly 312, to tighten arms 302 and 304 together around stem 153. During use, opening 314 is advanced over hanger 316 so that hanger 316 supports filter port 151 and attached container 112. If desired, hanger 316 can have substantially hard (i.e., about 90 degree) angles to facilitate keeping inlet port 151 and filter 170 in a generally vertical orientation. It is appreciated that opening 314 need not be located within hinge pin 307 but and otherwise be formed on clamp assembly 300.

Figure 17A:
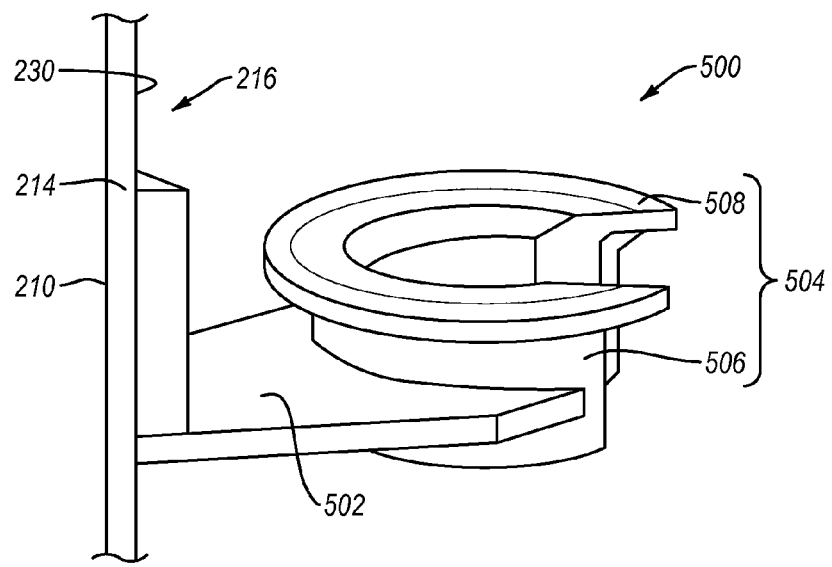
FIG. 17A is a perspective view of a hanger attached to the support housing.

In another embodiment, a removable attachment device can be used with a modified hanging flange and hanger. For example, as shown in FIG. 17A, hanger 316 can be replaced by a hanger 500 that is also secured to interior surface 230 of sidewall 214 at upper end 216 of receptacle 210. Hanger 500 includes a flange 502 attached to and projecting from sidewall 214 and a substantially C-shaped retainer 504 disposed at the end thereof. Retainer 504 includes a stem 506 and a flange 508 radially outwardly projecting therefrom. Both stem 506 and flange 508 have a substantially C-shaped configuration.

Figure 17B:
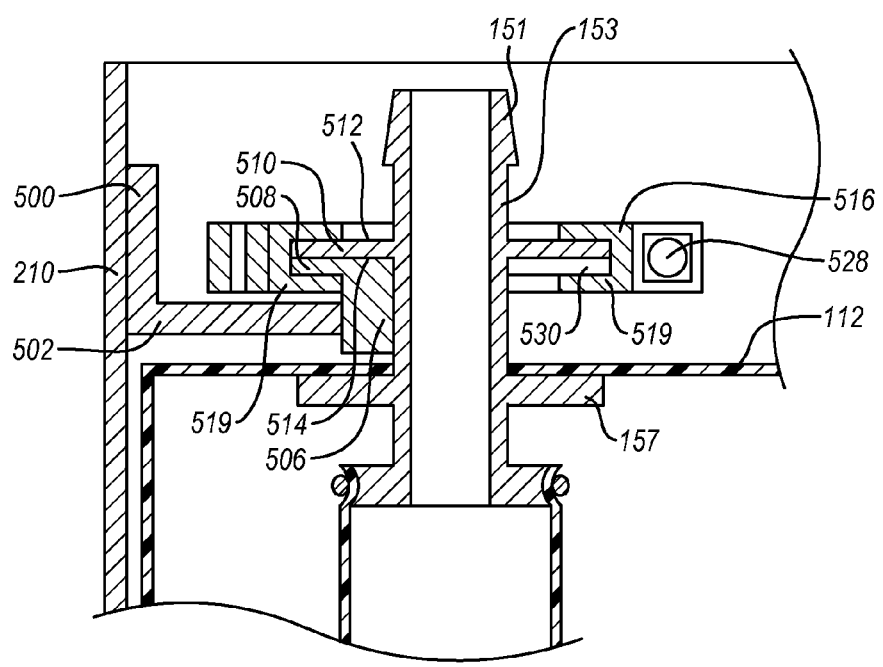
FIG. 17B is a cross sectional side view of a portion of a filter system showing another embodiment of an inlet port directly attached to the support housing the hanger shown in FIG. 17A.

Turning to FIG. 17B, a hanging flange 510 is integrally formed with stem 153 of inlet port 151. Hanging flange 510 is similar to hanging flange 292, discussed above, except that hanging flange 510 may omit openings extending therethrough, if desired, and is typically flat. Hanging flange 510 radially encircles and outwardly projects from stem 153 above flange 157. Hanging flange 510 has a top surface 512 and an opposing bottom surface 514. For receptacle 210 to support filter port 151, filter port 151 can be positioned so that stem 153 extends through stem 506 of support hanger 500 and the bottom surface 514 of hanging flange 510 rests upon flange 508 of hanger 500. In this position, hanger 500 can provide the desired support for container 112.

Figure 17C:
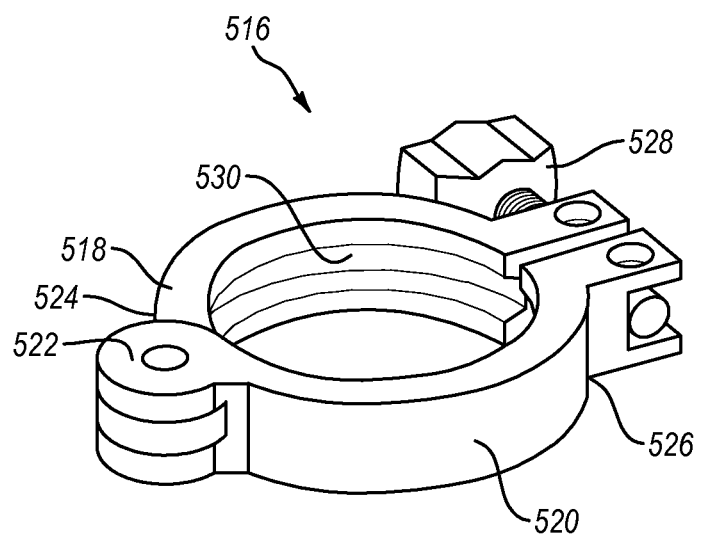
FIG. 17C is a perspective view of the clamp assembly shown in FIG. 17B.

To secure filter port 151 to hanger 500, a clamp assembly 516 can be used. Clamp assembly 516 can be similar to clamp assembly 300, discussed above, with a few differences. As shown in FIG. 17C, clamp assembly 516 includes a pair of mating arms 518 and 520 that rotate about a hinge 522 positioned at one end 524 of the pair of arms. At the other end 526 of the arms is a securing mechanism, such as a screw assembly 528, to tighten arms 518 and 520 together. An annular channel 530 is formed on the inside surface of arms 518 and 520.

Returning to FIG. 17B, to secure filter port 151 to support 500, arms 518 and 520 (collectively denoted as 519) are positioned around flange 508 and hanging flange 510 so that when clamp assembly 516 is closed and tightened, these structures are received within annular channel 530 and securely held together. A gasket or the like can also be positioned within annular channel 530, if desired, to form a more secure connection between clamp assembly 516 and flange 508 and hanging flange 510. Other types of securing methods and devices can alternatively be used to secure filter to receptacle 210.

Figure 19:
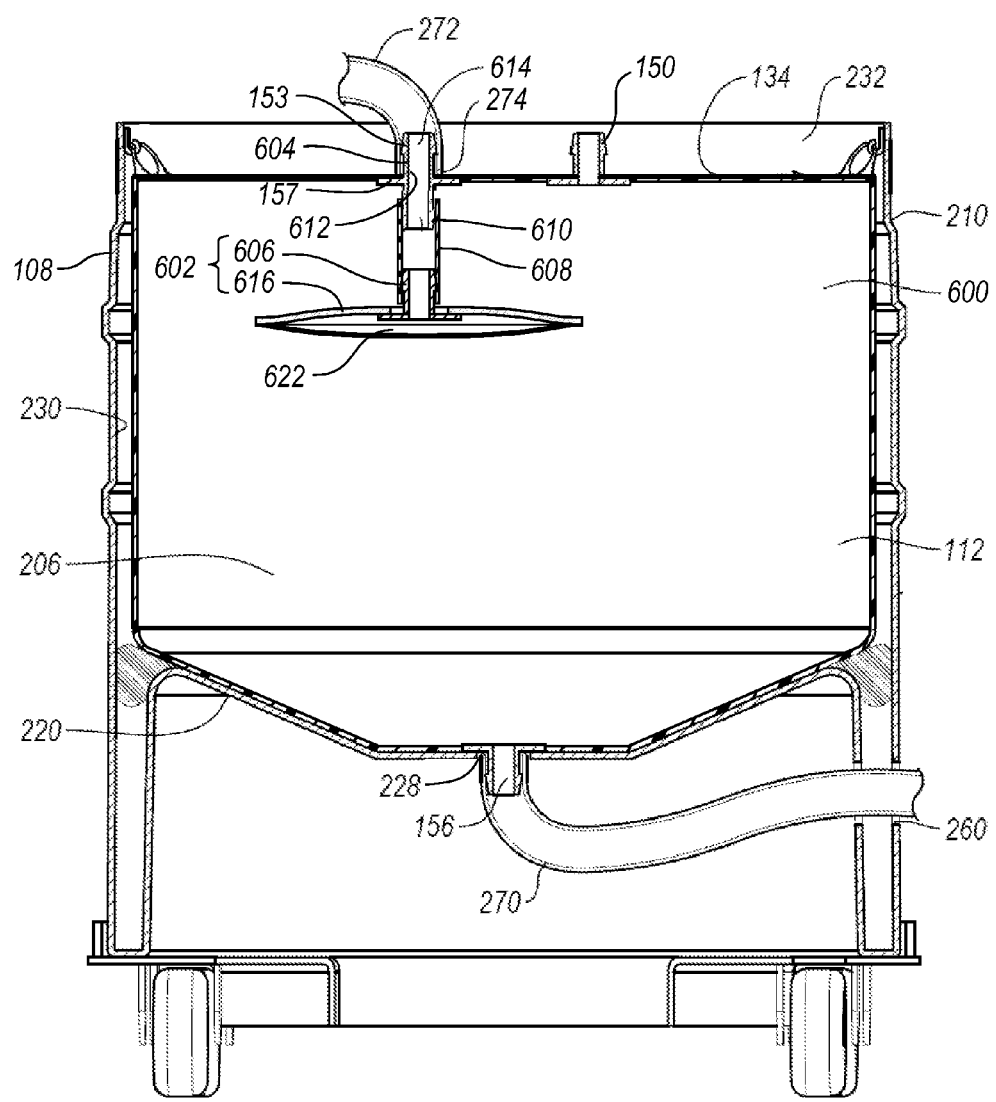
FIG. 19 is a cross sectional side view of a filter system in which another alternative embodiment of a filter assembly is disposed within the support housing.

FIG. 19 depicts another embodiment of a filter assembly 600. Like elements between filter assembly 600 and filter assembly 106 are identified by like reference characters. Similar to filter assembly 106, filter assembly 600 comprises a filter 602 disposed within container 112 and attached thereto using a filter port 604. However, instead of being directly attached to filter port 604, filter 602 includes an inlet port 606 that is attached to filter port 604 using a dip tube line 608.

Similar to filter port 151, filter port 604 includes barbed first stem 153 upwardly projecting from a top side of flange 157. A barbed second stem 610 projects from the bottom side of flange 157 so as to extend downward into compartment 126. Second stem 610 is generally similar to first stem 153 except that second stem 610 extends in the opposite direction from flange 157. Filter port 604 has an inside surface 612 that bounds a fluid passageway 614 extending therethrough, i.e., fluid passageway 614 extends through first stem 153, flange 157, and second stem 610. Filter port 604 can be integrally formed as a single unitary structure or can comprise two or more parts secured together.

Figure 20:
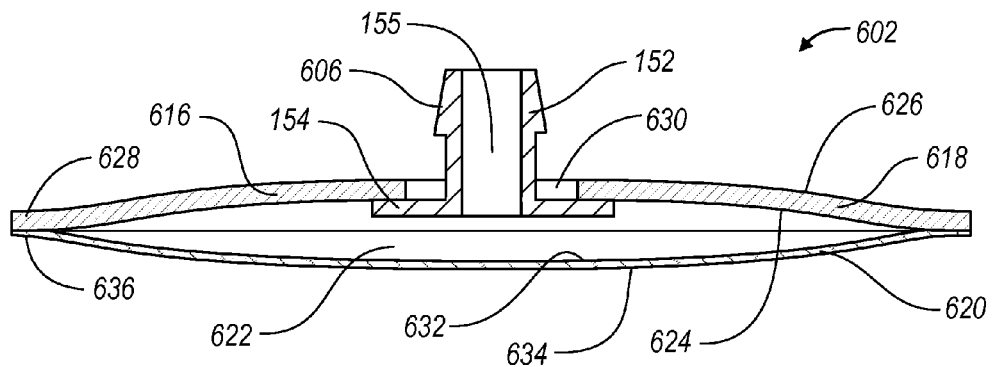
FIG. 20 is a cross sectional side view of the filter shown in FIG. 19.

Turning to FIG. 20, filter 602 comprises a two-dimensional pillow style bag 616 wherein two sheets 618 and 620 of material are placed in overlapping relation and the two sheets are bounded together at their peripheries to form an internal chamber 622.

Figure 21:
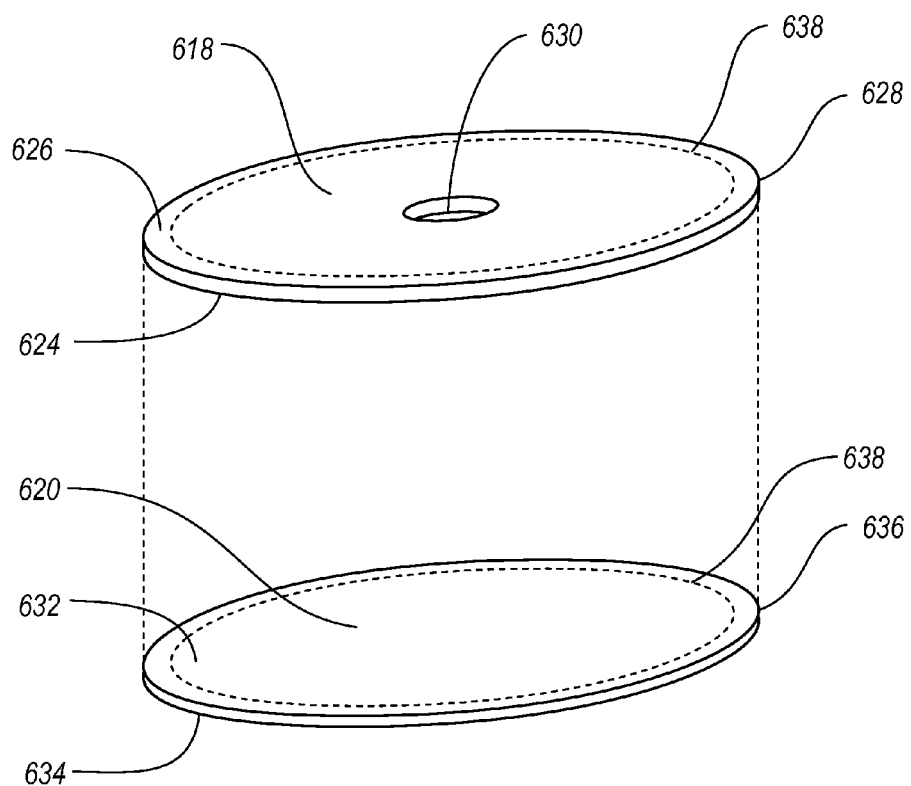
FIG. 21 is an exploded perspective view of a portion of the filter shown in FIG. 20.

Turning to FIG. 21 in conjunction with FIG. 20, sheet 618 has an interior surface 624 and an opposing exterior surface 626 extending to a perimeter edge 628. Sheet 618 is comprised of a flexible material such as polyethylene or other polymeric sheets, similar to body 120 of container 112. The material can be comprised of a single ply material or can comprise two or more layers which are either sealed together or separated to form a double wall container. Where the layers are sealed together, the material can comprise a laminated or extruded material. The laminated material comprises two or more separately formed layers that are subsequently secured together by an adhesive. Sheet 618 can be comprised of the same type of materials as discussed above with regard to body 120 of container 112. In one embodiment, sheet 618 is comprised of the same material as body 120. Although shown in the depicted embodiment as being substantially circular, it is appreciated that sheet 618 can have virtually any desired shape. Similarly, it is appreciated that sheet 618 can have virtually any desired size.

A hole 630 is formed in sheet 618 so as to extend therethrough between interior and exterior surfaces 624 and 626. Hole 630 is sized so as to be able to receive inlet port 606. Although hole 630 is shown in the depicted embodiment as being substantially centered on sheet 618, this is not required. Hole 630 can be positioned anywhere on sheet 618 and can be any size that will accommodate inlet port 606.

Sheet 620 has an interior surface 632 and an opposing exterior surface 634 extending to a perimeter edge 636. Sheet 620 is comprised of a flexible porous material that allows the cultured solution to pass through, yet prevents microcarriers from passing through. For example, sheet 620 can be comprised of a mesh material made of a polymeric material, such as those materials discussed above with respect to filter 170. Other polymeric and non-polymeric materials can also be used. Furthermore, pore size ranges of the mesh can be similar to those discussed above with respect to filter 170. Sheet 620 can be expandable and/or resiliently stretchable, if desired. Sheet 620 is generally sized and shaped to match the size and shape of sheet 618, although this is not required.

Inlet port 606 is similar to inlet ports 150 positioned on body 120 (see FIG. 19). As such, as shown in FIG. 20, inlet port 606 comprises a barbed tubular stem 152 having a flange 154 radially encircling and outwardly projecting therefrom. Inlet port 606 bounds a fluid passageway 155 that extends therethrough. During assembly, hole 630 is made through sheet 618 for the port. Stem 152 of inlet port 606 is then passed up through hole 630 until flange 154 rests against interior surface 624 of sheet 618. Conventional welding or other sealing techniques are then used to seal flange 154 to sheet 618.

After inlet port 606 has been secured to sheet 618, interior surfaces 624 and 632 of sheets 618 and 620 are positioned against each other, as shown in FIG. 20, and corresponding perimeter edges 628 and 636 are attached or secured together using heat energies, RF energies, sonics, or other sealing energies. Adhesives or other types of securing or attaching devices or methods can also be used. Dashed lines 638 of FIG. 21 depicts the perimeter portions of sheets 618 and 620 that are secured together during assembly. When secured, inside surfaces 624 and 632 together bound compartment 622, with material being deliverable thereinto via inlet port 606.

Returning to FIG. 19, once filter 602 has been assembled, filter 602 can be positioned within container 112. That is, during assembly of filter assembly 600, stem 152 of filter 602 can be fluidly coupled with second stem 610 of filter port 604 using dip tube line 608. Container 112 can then be sealed closed.

Similar to filter assembly 106, filter assembly 600 can be positioned before use within first chamber 232 of receptacle 210, and the top of container 112 can be attached to receptacle 210 using hanging tabs or other hanging elements. Also similar to filter assembly 106, outlet tube 270 can be connected to outlet port 156 and extended through central opening 228 and out from support housing 108 through access port 260.

During use, inlet tube 272 is coupled with bioreactor 102 (FIG. 1) so that a mixture of cultured solution and associated microcarriers can be introduced into inlet chamber 622. The cultured solution portion of the mixture passes through filter 602 and into outlet chamber 206, where the fluid can collect or exit container 112 through outlet port 156 and outlet tube 270. Filter 602 causes the microcarriers to be retained within inlet chamber 622 to be discarded or recycled for further use.

Figure 22A:
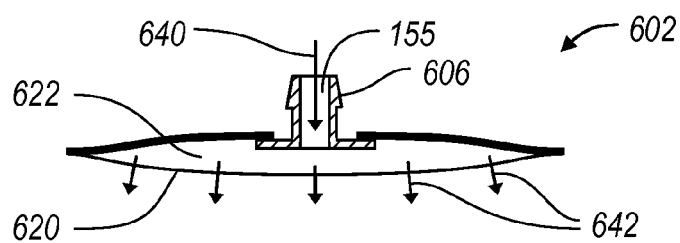
FIGS. 22A-22C are cross sectional side views of the filter assembly shown in FIG. 19, showing fluid flow through the filter during various stages of use.
Figure 22B:
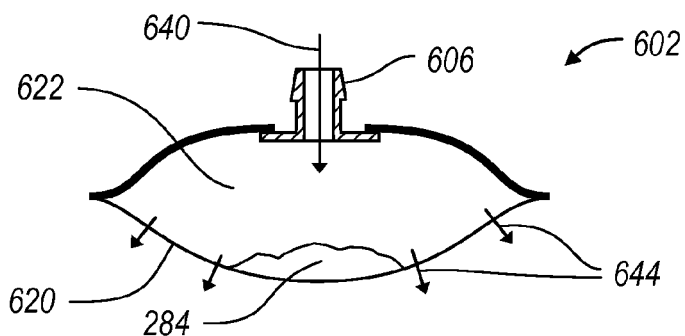
Figure 22C:
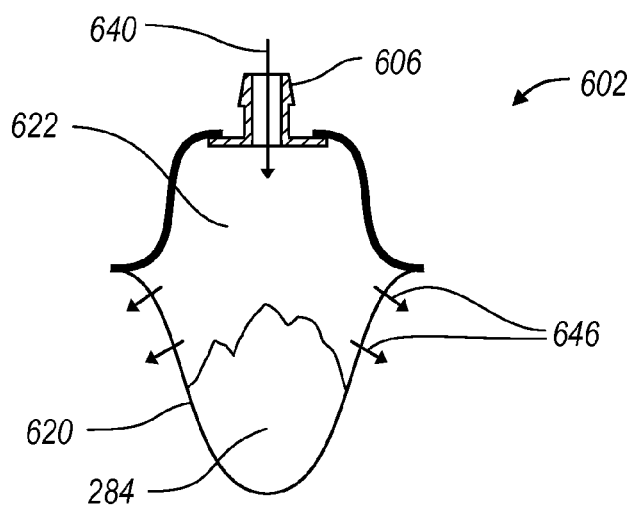

More specifically, the mixture passes through filter port 604 and dip tube line 608 to arrive at filter 602. The mixture passes through inlet port 606 and is received by inlet chamber 622 through fluid passageway 155, as depicted in FIGS. 22A-22C. As shown in FIG. 22A, as the mixture is first received within inlet chamber 622 as denoted by arrow 640, inlet chamber 622 is completely or mostly devoid of microcarriers and the cultured fluid can pass through porous sheet 620 through the bottom thereof, as indicated by arrows 642. Filter bag 602 can be substantially flat, as there is no weight to push it downward.

As shown in FIG. 22B, as more mixture flows into inlet chamber 622, the microcarriers 284 within the mixture are retained and begin to accumulate at the bottom of inlet chamber 622. The weight of the microcarriers 284 can cause filter 602 to elongate and extend further downward. The cultured solution continues to pass through porous sheet 620. However, the majority of the fluid passes out through the side portions of porous sheet 620 that is above the accumulated microcarriers, as shown by arrows 644.

As shown in FIG. 22C, as more microcarriers 284 continue to accumulate at the bottom portion of filter 602, the weight of the microcarriers may cause filter 602 to further elongate and fluid can continue to flow through the upper portion of sheet 620 not covered by microcarriers, as denoted by arrows 646. If an expandable material is used for porous sheet 620, the weight of the microcarriers can cause porous sheet 620 to expand further downward. This expansion can increase the surface area of porous sheet 620 which can allow for more cultured solution to flow through the sides of porous sheet 620 and more microcarriers can be retained.

Figure 23A:
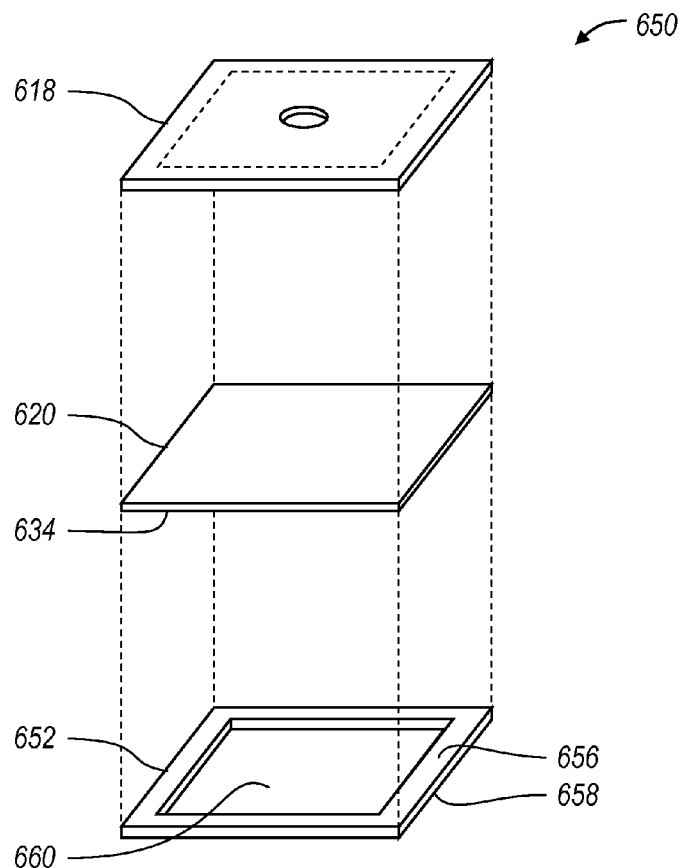
FIG. 23A is an exploded perspective view of an alternative filter sheet configuration that can be used in the filter assembly shown in FIG. 19.
Figure 23B:
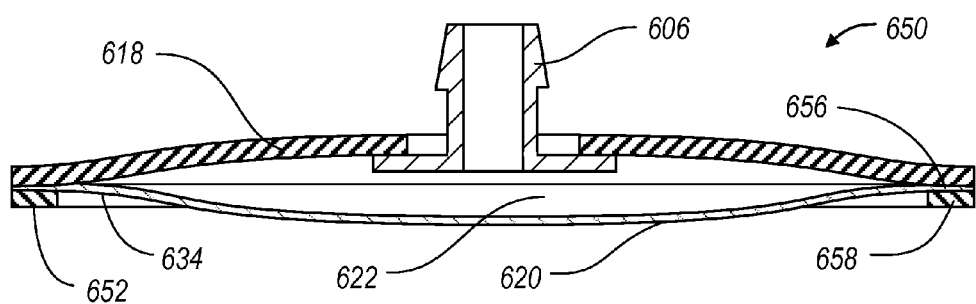
FIG. 23B is a cross sectional side view of a filter that incorporates the filter sheet configuration shown in FIG. 22A.

FIGS. 23A and 23B depict another embodiment of a filter 650 based on filter 602 but using an alternative filter sheet configuration. The sheets of filter 650 are depicted as being rectangular. However, as discussed above, this is exemplary only and the sheets can be of any size and shape. Similar to filter 602, filter 650 also includes flexible sheet 618 and porous sheet 620. However, filter 650 also includes a picture-frame sheet 652 positioned against exterior surface 634 of porous sheet 620 so as to sandwich the edges of porous sheet 620 between sheets 618 and 652, as particularly shown in FIG. 23B. Sheet 652 has an interior surface 656 and an opposing exterior surface 658. Sheet 652 bounds an opening 660 extending through sheet 652 between interior and exterior surfaces 656 and 658. Sheet 652 can be comprised of similar materials as sheet 618 and can be used to aid in securing porous sheet 620 to sheet 618. That is, sheet 652 may be useful if the porous material does not form a secure attachment to sheet 618. Sheet 652 can provide a better attachment to sheet 618 and the edges of sheet 620 can be better attached due to its being sandwiched between sheets 618 and 652.

Figure 23C:
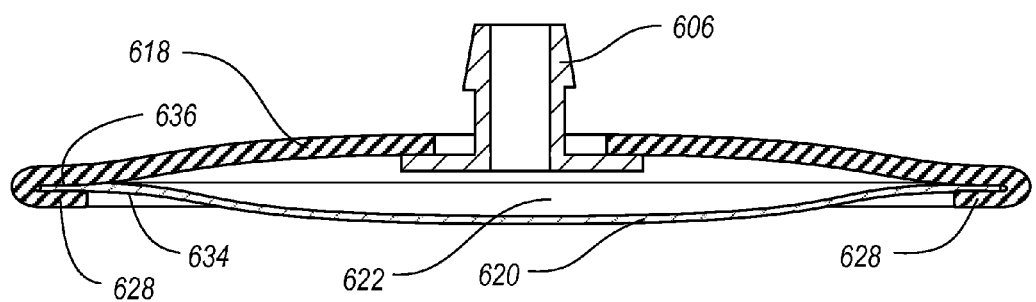
FIG. 23C is a cross sectional side view of a filter that incorporates another alternative filter sheet configuration.

In an alternative embodiment, shown in FIG. 23C, sheet 652 can be omitted and sheet 618 can be sized to be larger than sheet 620. The portion of perimeter edge 628 of sheet 618 that extends beyond perimeter edge 636 of sheet 620 can be folded over perimeter edge 636 so as to rest against exterior surface 634 of porous sheet 620 and form the picture-frame.

Figure 24B:
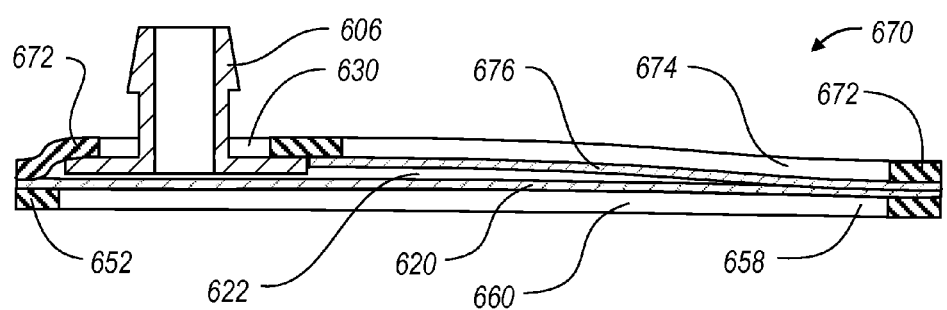
FIG. 24B is a cross sectional side view of a filter that incorporates the filter sheet configuration shown in FIG. 23A.
Figure 24A:
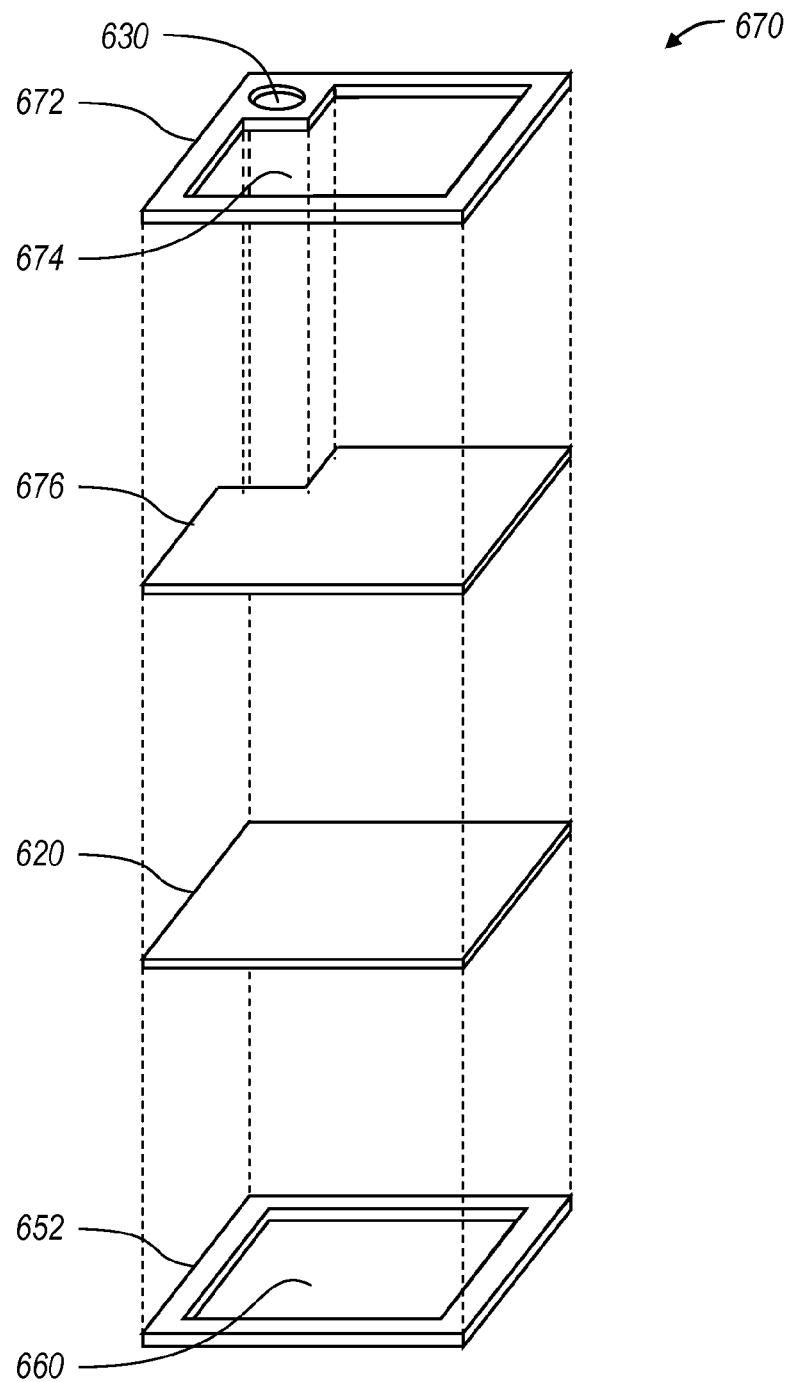
FIG. 24A is an exploded perspective view of another alternative filter sheet configuration that can be used in the filter assembly shown in FIG. 19.

FIGS. 24A and 24B depict another embodiment of a filter 670 based on filter 602 but using another alternative filter sheet configuration. Filter 670 is similar to filter 650, except that sheet 618 is replaced with a sheet 672 that bounds an opening 674 extending therethrough. To prevent microcarriers from passing through opening 674, another porous sheet 676 is also included to go along with porous sheet 620. Sheet 676 is sized similar to opening 674 and is secured to the interior surface of sheet 672. Porous sheet 676 does not cover hole 630 so that the cultured solution can pass through hole 630 and into internal chamber 622, which is now bounded by porous sheet 676 as well as sheets 672 and 620, as particularly shown in FIG. 24B. This embodiment provides more surface area for the solution to pass through than filters 602 or 650, as solution can also pass through porous sheet 676 covering opening 674 on top sheet 672. As shown in the depicted embodiment, hole 630 can be positioned near the perimeter edge of sheet 672 to allow opening 674 to have a larger surface area, if desired.

As with filter 650, picture frame sheet 652 can alternatively be omitted and sheet 672 can be sized to be larger than sheets 620 and 676. The portion of the perimeter edge of sheet 672 that extends beyond perimeter edge 636 of sheet 620 can be folded over perimeter edge 636 so as to rest against exterior surface 634 of porous sheet 620 and form the picture-frame in a manner similar to that discussed above with regard to filter 650.

As with filter port 151, filter port 604 can also be directly attached to receptacle 210 instead of or in conjunction with the hanging tabs and hangers, as discussed above with reference to FIGS. 9-10B and 17A-17C. It is appreciated that the filter embodiments shown in FIGS. 20-24B are exemplary only and that other two-dimensional pillow style bags can also be used. It is also appreciated that instead of using a dip tube line 608 to attach filter port 604 to inlet port 606, a single port can be used to directly attach top sheet 618 or 672 to body 120 of container 112.

Figure 11:
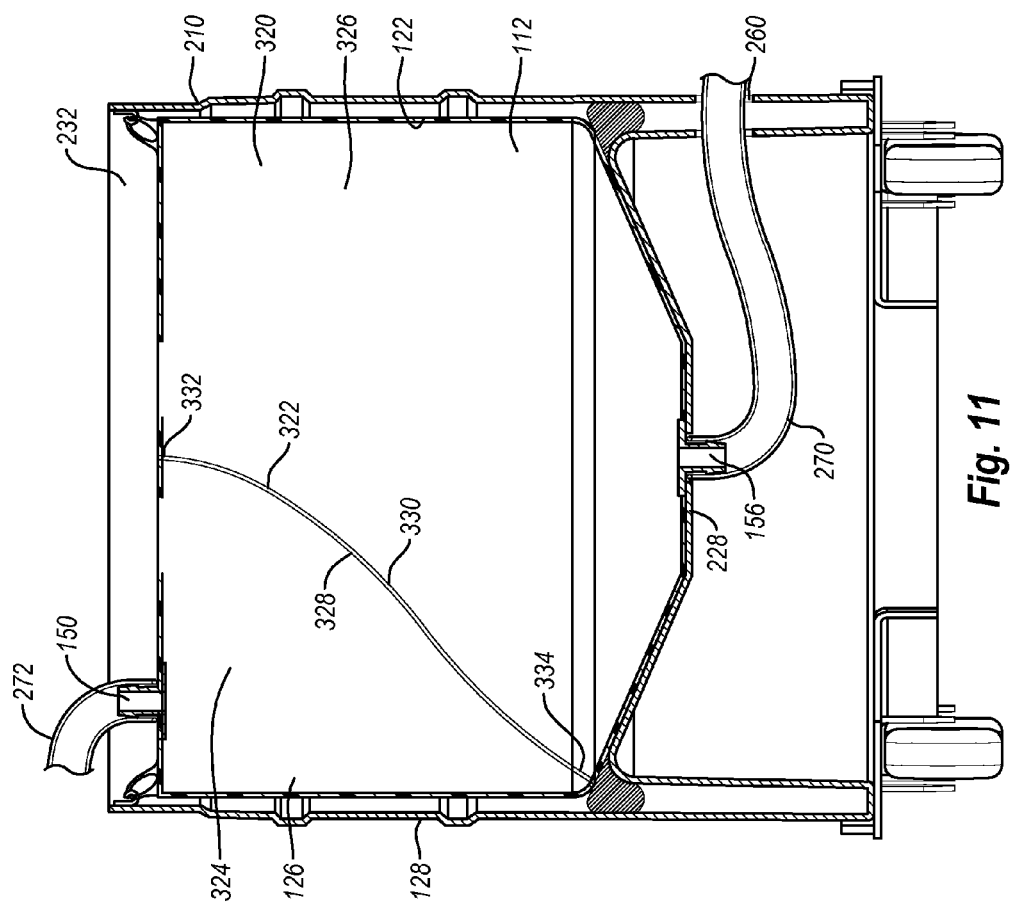
FIG. 11 is a cross sectional side view of a filter system in which an alternative embodiment of a filter assembly is disposed within the support housing.

FIG. 11 depicts another embodiment of a filter assembly 320. Like elements between filter assembly 320 and filter assembly 106 are identified by like reference characters. Filter assembly 320 includes a filter 322 that attaches directly or indirectly to the body 120 of container 112 to divide compartment 126 into an inlet chamber 324 and an outlet chamber 326. Filter 322 comprises a sheet of a porous material that will allow the cultured solution to pass therethrough but will prevent the microcarriers from passing therethrough. Filter 320 can be comprised of a sheet of the same materials as discussed above with regard to filter 170. Furthermore, filter 322 can be expandable and/or resilient, if desired. Filter 322 can be attached to or integrally formed with container 112.

In embodiments in which body 120 is comprised of two or more panels, filter 322 can be attached to body 120 by placing filter 322 between the panels so that as the panels are welded together, filter 322 is concurrently welded therebetween. For example, if container 122 is a pillow style bag which is comprised of two overlying panels, filter 322 can be placed between the overlying panels. As the perimeter edges of the panels are welded together to form the bag, filter 322 is concurrently secured to or welded into the weld matrix so that filter 322 bisects the compartment of the pillow bag. This method is particularly useful where filter 322 is comprised of a perforated sheet of a polymeric material but can also be used with netting and other materials. In an alternative method, a perimeter edge of filter 322 can be secured on a face of a first panel by welding, adhesive, or the like. A second panel can then overlay the first panel and the second panel welded to the first panel either over top of or adjacent to filter 322. In embodiments where container 122 is comprised of three or more panels, portions of filter 322 can be welded between different panels. Likewise, where container 122 comprises an extruded tube and opposing end panels, filter 322 can be welded or otherwise secured between the tube and one of the end panels or can be secured to one of the tube or the end panels and then the tube and end panel secured together.

Continuing with FIG. 11, filter 322 has an inlet surface 328 and an opposing outlet surface 330 that extend from a first end 332 at top end wall 134 of container 112 to a second end 334 at bottom end wall 136 or side wall 128 of container 112. Inlet chamber 324 is bounded by the interior surface 122 of a portion of container 112 and inlet surface 328 of filter 322, and outlet chamber 326 is bounded by the interior surface 122 of the remaining portion of container 112 and outlet surface 330 of filter 322. Inlet port 150 is positioned on top end wall 134 so as to fluidly communicate with inlet chamber 324 and outlet port 156 is positioned on bottom end wall 136 so as to fluidly communicate with outlet chamber 326. As such, fluid passes through filter 322 as it moves between inlet and outlet ports 150 and 156.

Similar to filter assembly 106, filter assembly 320 also incorporates receptacle 210 into which container 112 is received. As such, similar to filter assembly 106, filter assembly 320 can also be configured in different shapes, as discussed above and can include hanging tabs and hangers, as discussed above with respect to filter assembly 106. In this embodiment, however, inlet port 150 would function as filter port 151 with regard to being modified or otherwise connected to receptacle 210 as discussed above with respect to filter port 151.

Filter 322 is typically comprised of a sheet of flexible material but could be comprised of a sheet of rigid or semi-rigid material. As such, filter 322 can be substantially planar or have one or more curves between first and second ends 332 and 334. Furthermore, filter 322 can be substantially taut or substantially loose. In the depicted embodiment, first end 332 of filter 322 is positioned at about the middle of top end wall 134 and second end 334 is positioned at bottom end wall 136 adjacent side wall 128. Other configurations are also possible. For example, first end 332 of filter 322 can be positioned on top end wall 134 nearer side wall 128, if desired. Also, first end 332 or second end 334 or both can be positioned on side wall 128 instead of top and bottom end walls 134 and 136. Regardless of the positioning of first and second ends 332 and 334 of filter 322, however, filter 322 is positioned such that inlet port 150 directly fluidly communicates with inlet chamber 324 and outlet port 156 directly fluidly communicates with outlet chamber 326.

Similar to filter assembly 106, filter assembly 320 can be positioned before use within first chamber 232 of receptacle 210, and the top of container 112 can be attached to receptacle 210 using hanging tabs or other hanging elements. Also similar to filter assembly 106, outlet tube 270 can be connected to outlet port 156 and extended through central opening 228 and out from support housing 108 through access port 260, as shown in FIG. 11.

During use, inlet tube 272 is coupled with bioreactor 102 (FIG. 1) so that a mixture of cultured solution and associated microcarriers can be introduced into inlet chamber 324 therethrough. The cultured solution portion of the mixture passes through filter 322 and into outlet chamber 326, where the fluid can collect or exit container 112 through outlet port 156 and outlet tube 270. Filter 322 causes the microcarriers to be retained within inlet chamber 324 to be discarded or recycled for further used.

Figure 12A:
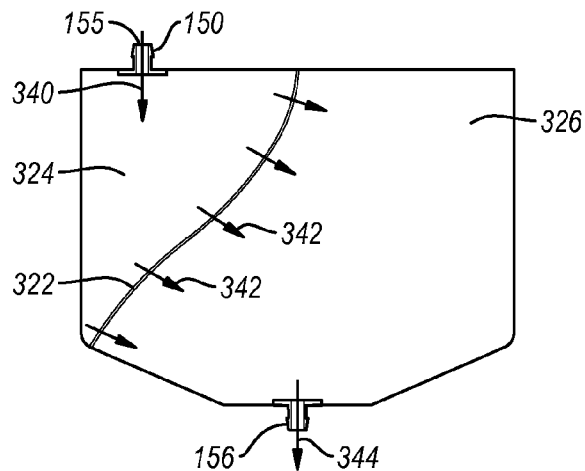
FIGS. 12A-12C are cross sectional side views of the filter assembly shown in FIG. 11, showing fluid flow through the filter during various stages of use.
Figure 12B:
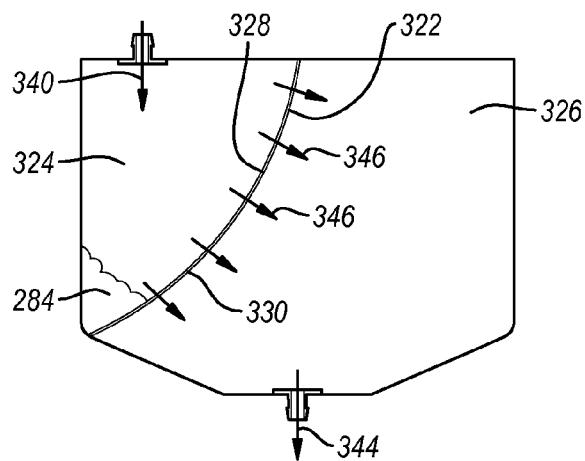
Figure 12C:
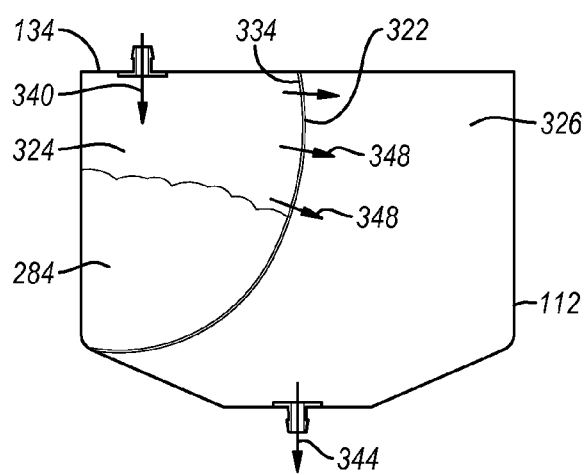

More specifically, the mixture passes through inlet port 150 and is received by inlet chamber 324 through fluid passageway 155, as depicted in FIGS. 12A-12C. As shown in FIG. 12A, as the mixture is first received within inlet chamber 324, as denoted by arrow 340, inlet chamber 324 is completely or mostly devoid of microcarriers and the cultured fluid can pass through filter 322 along its entire length into outlet chamber 326, as indicated by arrows 342. The cultured fluid can then pass out of outlet chamber 326 through outlet port 156, as denoted by arrow 344.

As more mixture flows into inlet chamber 324, the microcarriers 284 begin to accumulate at the bottom of inlet chamber 324 as the cultured fluid continues to pass through filter 322, as shown by arrows 346 and 348 in FIGS. 12B and 12C. As can be seen, because second end 334 of filter 322 extends to and is supported by top end wall 134 of container 112, fluid can continue to flow through the upper portion of filter 322 not covered by microcarriers, as denoted by arrows 348, even as more microcarriers may accumulate at the bottom portion of filter 322. If an expandable material is used for filter 322, the weight of the microcarriers can cause filter 322 to expand downward and outward, as depicted in FIGS. 12B and 12C. This expansion increases the surface area of side surfaces 328 and 330 (FIG. 11) of filter 322 which allows for more cultured solution to flow through the sides of filter 322 and more microcarriers to be retained.

Figure 13:
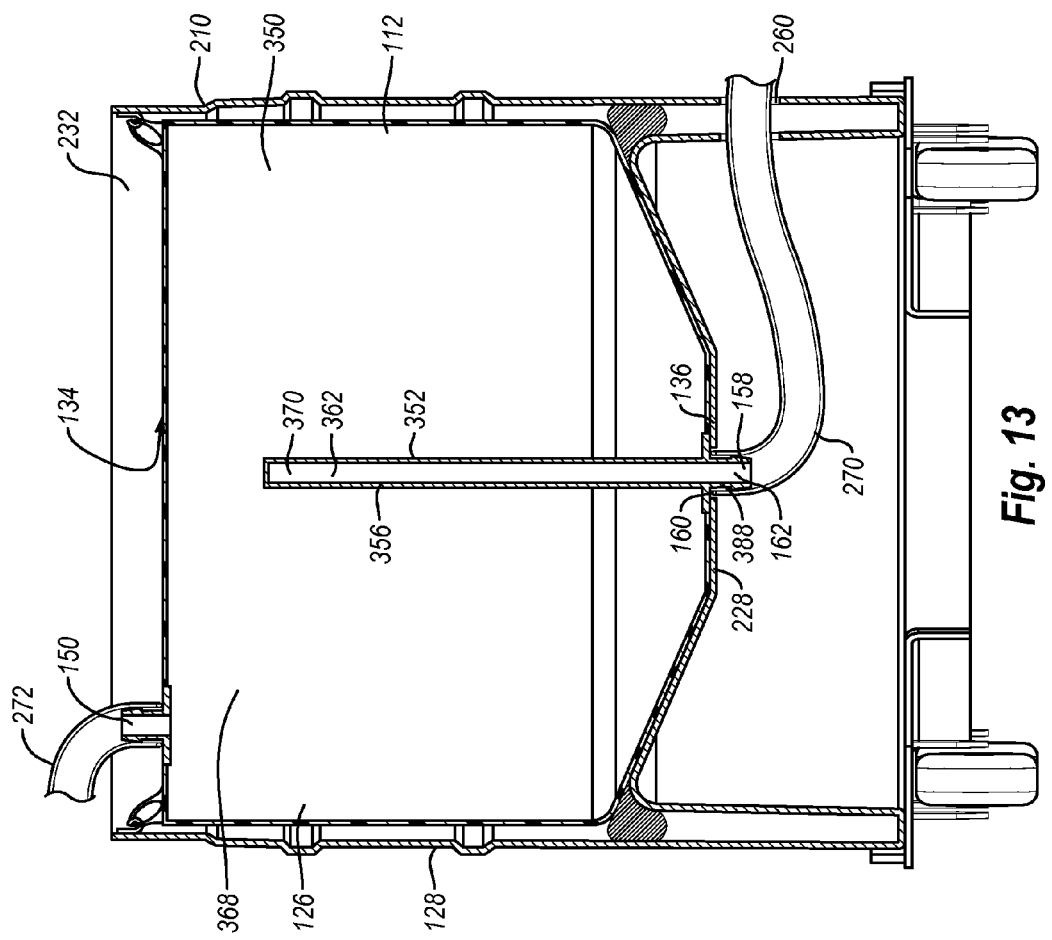
FIG. 13 is a cross sectional side view of a filter system in which another alternative embodiment of a filter assembly is disposed within the support housing.
Figure 14:
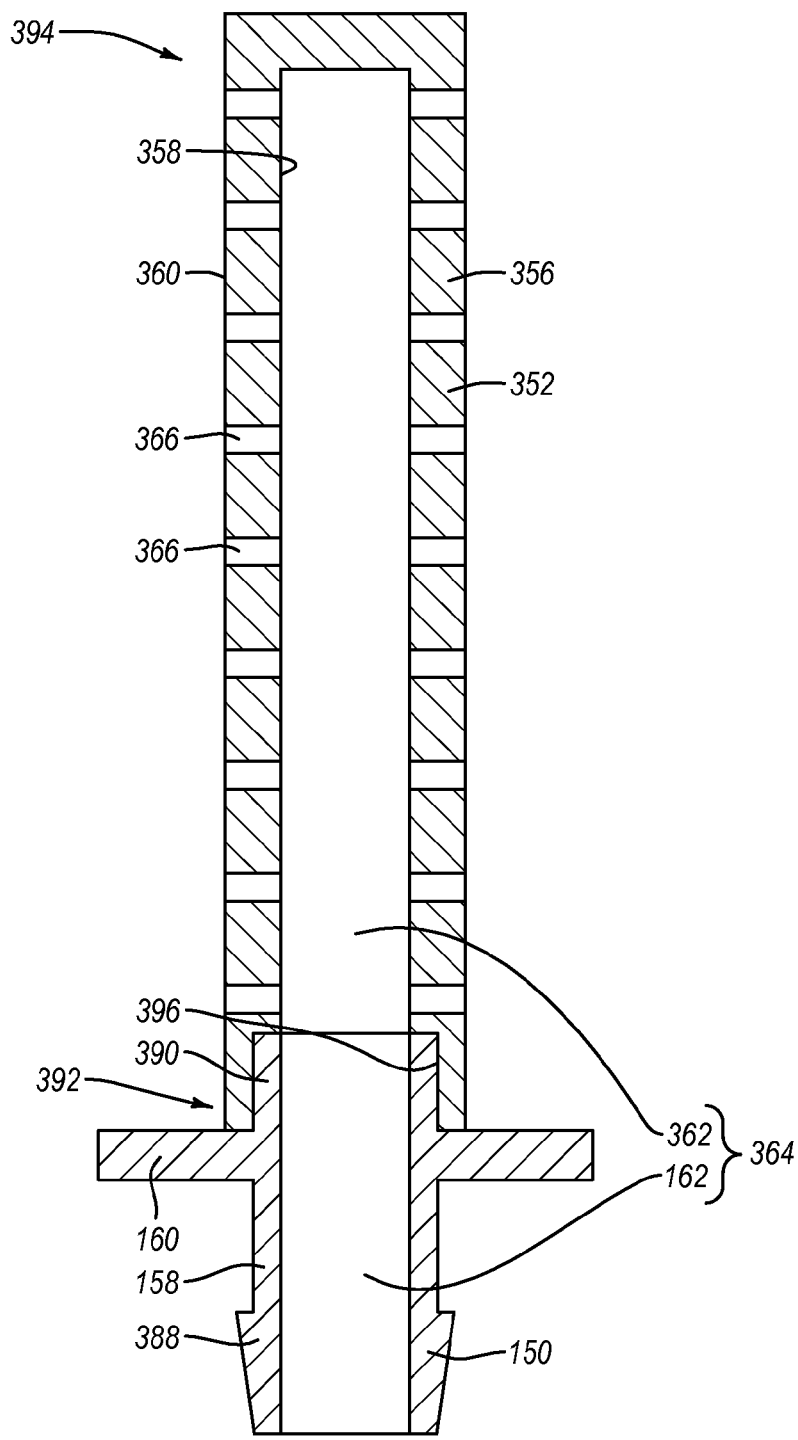
FIG. 14 is a cross sectional side view of the filter and outlet port of the filter assembly shown in FIG. 13.

FIG. 13 depicts another embodiment of a filter assembly 350 incorporating features of the present invention. Again, like elements between different embodiments are identified by like reference characters. Filter assembly 350 includes container 112 and a filter 352 coupled with an outlet port 388 so as to extend upward into compartment 126. Turning to FIG. 14, outlet port 388 is similar to outlet port 156 but has an additional stem 390 extending upward from flange 160 (i.e., in the opposite direction from flange 160 as stem 158). Stem 390 is generally collinear with stem 158, although this is not required.

Filter 352 includes a sidewall 356 having an inside surface 358 and an opposing outside surface 360 extending from an open first end 392 to a spaced apart closed second end 394. Inside surface 358 of sidewall 356 bounds a fluid passageway 362 extending therethrough. The open first end 392 of filter 352 couples with stem 390 so that fluid passageways 162 and 362 fluidly couple with each other and combine to form fluid passageway 364. Stem 158, 390, and filter 352 can be substantially collinear, although that is not required. Filter 352 can attach to stem 390 by adhesive, welding, threaded connection, press fit, crimping or other known connecting method. In addition, if desired, a channel 396 can be formed on the inside surface 358 at first end 392 of filter 352 to aid in attaching to stem 390, as in the depicted embodiment.

A plurality of openings 366 extend through sidewall 356 of filter 352 that are large enough to allow the cultured solution to flow through, but small enough to prevent the microcarriers from flowing through. The openings 366 can encircle and extend all along filter 352 or any portion thereof. In one embodiment, filter 352 comprises a stem that is substantially rigid so as to prevent filter 352 from collapsing as microcarriers build up around it. For example, filter 352 can be comprised of plastic, metal, composite, glass or the like. Openings 366 can be formed as part of a molding process or can subsequently be drilled or otherwise formed. Other methods for forming openings 366 can also be used.

As shown in FIG. 13, during assembly, a hole is formed in bottom end wall 136. Outlet port 156 is seated within the hole so that filter 352 extends upward into compartment 126 and flange 160 rests against bottom end wall 136. Similar to other outlet ports discussed herein, conventional welding or other sealing technique can then be used to seal flange 160 to bottom end wall 136.

Similar to other embodiments discussed herein, filter 352 divides compartment 126 into two separate chambers—an inlet chamber 368 and an outlet chamber 370. Fluid passageway 362 corresponds to outlet chamber 370. Thus, outlet chamber 370 is fluidly coupled with fluid passageway 162 of outlet port 156. Inlet chamber 368 is the portion of compartment 126 external to outlet chamber 370. Fluid flows from inlet chamber 368 to outlet chamber 370 through filter 352, as discussed below.

As noted above, when outlet port 156 is attached to container 112, filter 352 extends upward into compartment 126. Filter 352 can extend as far upward into compartment 126 as desired. In some embodiments, filter 352 has a length that allows it to contact and, if desired, attach to top end wall 134 of container 112. Other lengths are also possible. Filter 352 can be attached to outlet port 156 by adhesive, threaded connection or other attachment method. Alternatively, filter 352 can be integrally formed with outlet port 156.

Similar to the filter assemblies discussed above, filter assembly 350 can be positioned before use within first chamber 232 of receptacle 210, and the top of container 112 can be attached to receptacle 210 using hanging tabs or other hanging elements. Also similar to the filter assemblies discussed above, outlet tube 270 can be connected to outlet port 156 and extended through central opening 228 and out from support housing 108 through access port 260, as shown in FIG. 13.

Inlet tube 272 is also attached to inlet port 150 and extends to bioreactor 102 (FIG. 2). During use a mixture of cultured solution and associated microcarriers are introduced into inlet chamber 368 through inlet port 150. The cultured solution passes through the openings 366 (FIG. 14) in the sidewall 356 of filter 352 and into outlet chamber 370. The fluid flows down through fluid passageway 162 of outlet port 156 where the fluid can exit container 112 through outlet tube 270. The microcarriers, which cannot pass through filter 352, collect at the bottom of container 112.

Figure 15A:
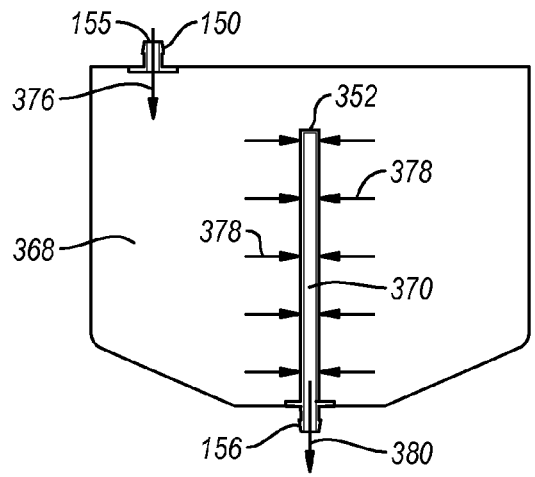
FIGS. 15A-15C are cross sectional side views of the filter assembly shown in FIG. 13, showing fluid flow through the filter during various stages of use.
Figure 15B:
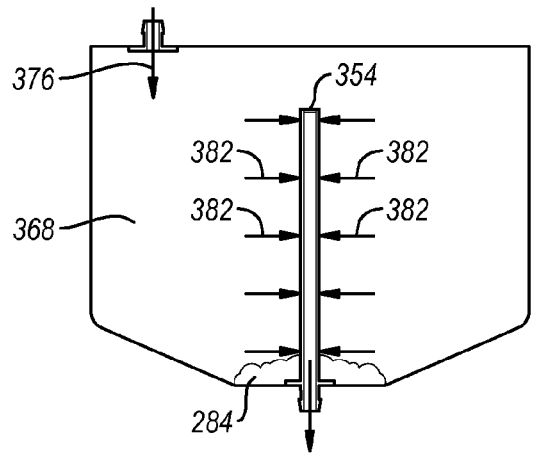
Figure 15C:
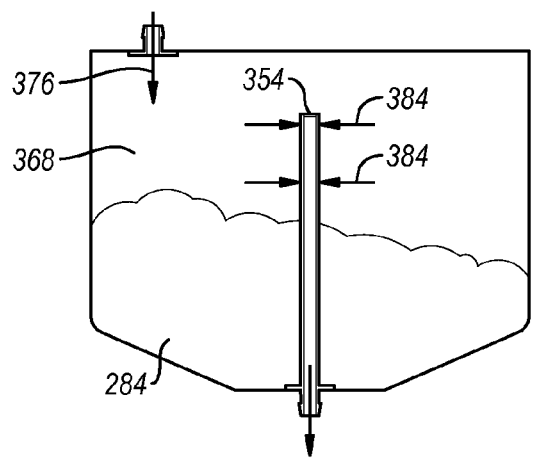

More specifically, the mixture passes through inlet port 150 and is received by inlet chamber 368 through fluid passageway 155, as depicted in FIGS. 15A-15C. As shown in FIG. 15A, as the mixture is first received within inlet chamber 368, as denoted by arrow 376, inlet chamber 368 is completely or mostly devoid of microcarriers and the cultured fluid can pass through filter 352 along its entire length into outlet chamber 370, as indicated by arrows 378. The cultured fluid can then pass out of outlet chamber 370 through outlet port 156, as denoted by arrow 380. As more mixture flows into inlet chamber 368, the microcarriers 284 begin to accumulate at the bottom of inlet chamber 368 as the cultured fluid continues to pass through the filter 352, as shown by arrows 382 and 384 in FIGS. 15B and 15C. As can be seen, however, as long as filter 352 extends upward beyond the retained microcarriers 284, fluid can continue to flow through the upper portion of filter 352, as denoted by arrows 384 even as more microcarriers may accumulate at the bottom portion of filter 352. That is, because filter 352 extends vertically within container 112, at least a portion of filter 352 remains openly exposed to receive the cultured solution even when a lower portion of filter 352 may be covered by microcarriers.

After use, filter assembly 350 can be discarded with the microcarriers. Alternatively, container 112 can be opened and the microcarriers recycled.

Figure 16:
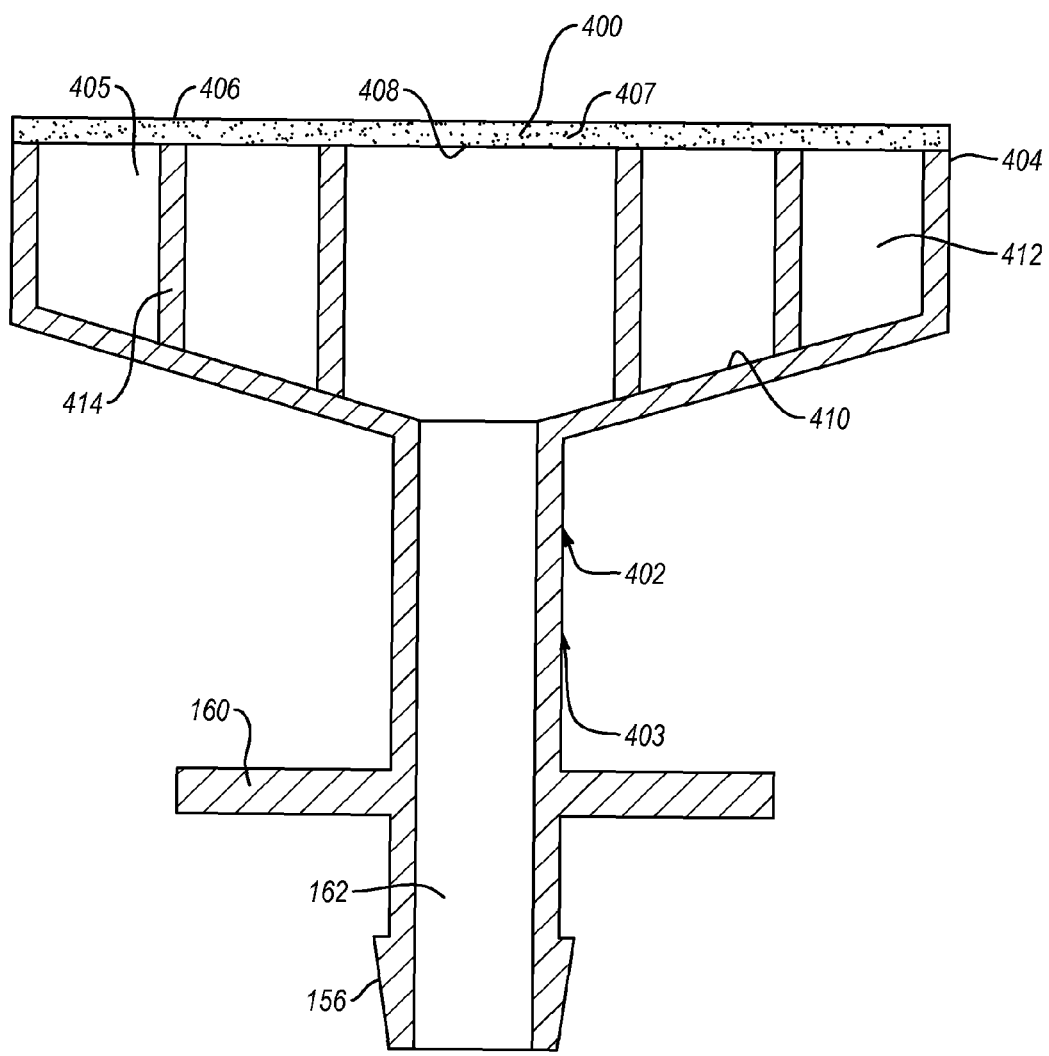
FIG. 16 is a cross sectional side view of an alternative embodiment of a filter/outlet port combination.

FIG. 16 depicts another embodiment of a filter 400 that can be used in place of filter 352 in filter assembly 350. Similar to filter 352, filter 400 also attaches to outlet port 156. However, instead of being substantially vertical, filter 400 is substantially horizontal. To accommodate filter 400, outlet port 156 includes a stem 402 that extends from a proximal end 403 at flange 160 to a spaced apart distal end 404. The distal end 404 of stem 402 flairs out radially so as to be wider than at the proximal end 403 and has an opening 405 at distal end 404.

A filtering element 407 is positioned over the opening 405 at the distal end 404 of stem 402. Filtering element 407 has an outer surface 406 and an opposing inner surface 408 and can be made of any of the filtering materials discussed above. Thus, filtering element 407 permits cultured solution which includes the detached cells to pass through filtering element 407 but prevents microcarriers from passing therethrough. Stem 402 has an interior surface 410 that together with the inner surface 408 of filtering element 407 bounds a compartment 412 that is directly coupled with fluid passageway 162 of outlet port 156. To accommodate for the weight of the microcarriers that may accumulate on the filtering material, a framework 414 can be positioned within compartment 412 to bolster filtering element 407 and prevent filtering element 404 from collapsing. Framework 414 can be comprised of intermingled struts and walls or can be a thick material through which fluid can pass. Regardless of its composition, framework 414 is configured to allow the cultured fluid to flow therethrough to outlet port 156. To aid in the flow of the fluid, interior surface 410 can be angled to guide the fluid to the fluid passageway 162.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A filter system for separating microcarriers from a fluid medium, the filter system comprising:
 a substantially rigid support housing having a floor with a side wall upstanding therefrom, the floor and the side wall bounding a chamber; and
 a filter assembly being removably disposable within the chamber of the support housing, the filter assembly comprising:
  a container bounding a sterile compartment adapted to hold a fluid;
  an inlet port through which fluid flows into the compartment, the inlet port being removably attachable to the support housing;
  an outlet port through which fluid flows out of the compartment; and
  a filter disposed within the compartment, the filter dividing the compartment into an inlet chamber that is fluidly coupled with the inlet port and an outlet chamber that is fluidly coupled with the outlet port, the filter allowing a medium to pass therethrough but preventing microcarriers disposed in the medium from passing therethrough, the filter comprising a porous bag or sock that bounds the inlet chamber, the porous bag or sock being coupled with the inlet port either directly or through a tube.

2. The filter system as recited in claim 1, wherein the container comprises a flexible bag.

3. The filter system as recited in claim 1, wherein the porous bag or sock is coupled with the inlet port by the tube.

4. The filter system as recited in claim 1, wherein the filter is expandable.

5. The filter system as recited in claim 1, wherein the filter is flexible.

6. The filter system as recited in claim 1, wherein the filter is comprised of a mesh material or a perforated polymeric sheet.

7. The filter system as recited in claim 1, wherein the filter is coupled with the inlet port so that any fluid medium passing through the inlet port passes through the filter.

8. The filter system as recited in claim 1, wherein the filter comprises:
 a plurality of sheets, at least one of the sheets being comprised of a porous material, the plurality of sheets being bounded together at their peripheries to form the inlet chamber; and
 a filter inlet port through which fluid flows into the inlet chamber, the filter inlet port extending through at least one of the plurality of sheets, the filter inlet port being fluidly coupled with the inlet port.

9. The filter system as recited in claim 1, wherein the container has a floor and the filter is suspended above the floor.

10. The filter system as recited in claim 1, wherein the container is removably attachable to an upper end of the support housing.

11. A filter system for separating microcarriers from a medium in which the microcarriers have been added to aid in cell culture development, the filter system comprising:
 a support housing having a floor with a side wall upstanding therefrom, the floor and the side wall bounding a chamber; and
 a filter assembly being removably disposable within the chamber of the support housing, the filter assembly comprising:
  a container bounding a sterile compartment adapted to hold a fluid;
  a filter port attached to the container, the filter port having a fluid passageway extending therethrough such that a cultured solution having microcarriers therein can pass therethrough; and
  a filter disposed within the sterile compartment and coupled to the filter port so as to fluidly communicate with the fluid passageway of the filter port, the filter comprising a porous bag or sock that bounds an inlet chamber and is being comprised of a porous material configured to allow a cultured solution that includes cells to pass therethrough while preventing microcarriers from passing therethrough; and an inlet port attached to the porous bag or sock, the inlet port being fluid coupled with the filter port and being removably attached to the support housing.

12. The filter system as recited in claim 11, further comprising an outlet port attached to the container, the outlet port having a fluid passageway extending therethrough such that the cultured solution can exit the sterile compartment therethrough.

13. The filter system as recited in claim 11, wherein the filter comprises:
   a plurality of sheets, at least one of the sheets being comprised of a porous material, the plurality of sheets being bounded together at their peripheries to form the inlet chamber; and
   a filter inlet port through which fluid flows into the inlet chamber, the filter inlet port extending through at least one of the plurality of sheets, the filter inlet port being fluidly coupled with the filter port.

14. The filter system as recited in claim 13, wherein the filter inlet port is fluidly coupled with the filter port by a tube.

15. The filter system as recited in claim 13, wherein the plurality of sheets comprises a first sheet and a second sheet bounded together at their peripheries, the second sheet being comprised of the porous material, the first and second sheets bounding the inlet chamber.

16. The filter system as recited in claim 15, wherein the plurality of sheets further comprises a third sheet having an opening extending therethrough, the third sheet being bounded to the first and second sheets at the periphery of the third sheet such that the second sheet is sandwiched between the first and third sheets at the periphery of the second sheet.

17. The filter system as recited in claim 15, wherein the first sheet has an opening extending therethrough, and the plurality of sheets further comprises a third sheet, the third sheet being comprised of the porous material, the third sheet being bounded to the first sheet to cover the opening therein, the third sheet also bounding the inlet chamber.

18. The filter system as recited in claim 15, wherein the perimeter edges of the first sheet are wrapped around the perimeter edges of the second sheet and bounded thereto.

19. A filter system for separating microcarriers from a medium in which the microcarriers have been added to aid in cell culture development, the filter system comprising:
   a support housing having a floor with a side wall upstanding therefrom, the floor and the side wall bounding a chamber; and
   a filter assembly being removably disposable within the chamber of the support housing, the filter assembly comprising:
      a flexible bag bounding a sterile compartment adapted to hold a fluid;
      a filter comprising a porous bag or sock comprised of a porous sheet of flexible material, the porous bag or sock bounding an inlet chamber;
      an inlet port coupled with the flexible bag and being removably attached to the support housing;
      a tube extending from the inlet port to the porous bag or sock so as to communicate with the inlet chamber; and
      an outlet port coupled with the flexible bag so as to communicate with the sterile compartment.

20. The filter system as recited in claim 11, further comprising a tube extending from the filter port to the inlet port.

* * * * *